(12) United States Patent
Quijano et al.

(10) Patent No.: US 10,076,410 B2
(45) Date of Patent: Sep. 18, 2018

(54) CATHETER-GUIDED REPLACEMENT VALVES APPARATUS AND METHODS

(71) Applicant: Navigate Cardiac Structures, Inc., Lake Forest, CA (US)

(72) Inventors: Rodolfo C. Quijano, Laguna Hills, CA (US); Jason K. Clark, Corona, CA (US)

(73) Assignee: NAVIGATE CARDIAC STRUCTURES, INC., Laguna Hills, CA (US)

( * ) Notice: Subject to any disclaimer, the term of this patent is extended or adjusted under 35 U.S.C. 154(b) by 228 days.

(21) Appl. No.: 14/777,433

(22) PCT Filed: Mar. 15, 2014

(86) PCT No.: PCT/US2014/030078
§ 371 (c)(1),
(2) Date: Sep. 15, 2015

(87) PCT Pub. No.: WO2014/145338
PCT Pub. Date: Sep. 18, 2014

(65) Prior Publication Data
US 2016/0030171 A1    Feb. 4, 2016

Related U.S. Application Data

(60) Provisional application No. 61/802,311, filed on Mar. 15, 2013.

(51) Int. Cl.
*A61F 2/24*    (2006.01)
*A61F 2/966*   (2013.01)
(Continued)

(52) U.S. Cl.
CPC ............ *A61F 2/2418* (2013.01); *A61F 2/243* (2013.01); *A61F 2/2436* (2013.01); *A61F 2/844* (2013.01);
(Continued)

(58) Field of Classification Search
CPC .......... A61F 2/24; A61F 2/243; A61F 2/2418; A61F 2/2436
(Continued)

(56) References Cited

U.S. PATENT DOCUMENTS 8,317,858 B2 * 11/2012 Straubinger .......... A61F 2/2418
623/1.15
2010/0121423 A1 * 5/2010 Bernhard .............. A61F 2/2418
623/1.2

FOREIGN PATENT DOCUMENTS

WO    2001/049213 A1    7/2001
WO    2008/150529 A1    12/2008
(Continued)

OTHER PUBLICATIONS

International Search Report of corresponding PCT Application No. PCT/US2014/030078 dated Jul. 2, 2014.

*Primary Examiner* — Vy Bui
(74) *Attorney, Agent, or Firm* — Kurt T. Mulville; VLP Law Group, LLP

(57) ABSTRACT

The present invention is a replacement mitral valve suitable for catheter-based deployment. The replacement mitral valve has structure and dimensions that are uniquely suited to engage the annulus surrounding the native mitral valve and to restore normal function to a diseased valve. The invention describes the structures and functions of a replacement mitral valve and methods that are adapted for minimally invasive, catheter-based deployment of the valve.

5 Claims, 16 Drawing Sheets

(51) Int. Cl.
*A61F 2/844* (2013.01)
*A61F 2/86* (2013.01)

(52) U.S. Cl.
CPC ......... *A61F 2/86* (2013.01); *A61F 2002/9665* (2013.01); *A61F 2210/0019* (2013.01); *A61F 2220/0016* (2013.01); *A61F 2230/0067* (2013.01)

(58) Field of Classification Search
USPC ... 623/1.12, 1.16, 1.2, 1.15, 1.24, 1.26, 1.36
See application file for complete search history.

(56) References Cited

FOREIGN PATENT DOCUMENTS

| | | |
|---|---|---|
| WO | 2009/106545 A1 | 9/2009 |
| WO | 2009/132187 A1 | 10/2009 |
| WO | 2010/008549 A1 | 1/2010 |
| WO | 2010/022138 A1 | 2/2010 |
| WO | 2010/127041 A1 | 11/2010 |
| WO | 2011/002996 A1 | 1/2011 |
| WO | 2011/069048 A1 | 6/2011 |
| WO | 2011/150399 A1 | 12/2011 |
| WO | 2011/163275 A1 | 12/2011 |
| WO | 2013/0053950 A1 | 2/2013 |
| WO | 2014/145338 A1 | 9/2014 |

* cited by examiner

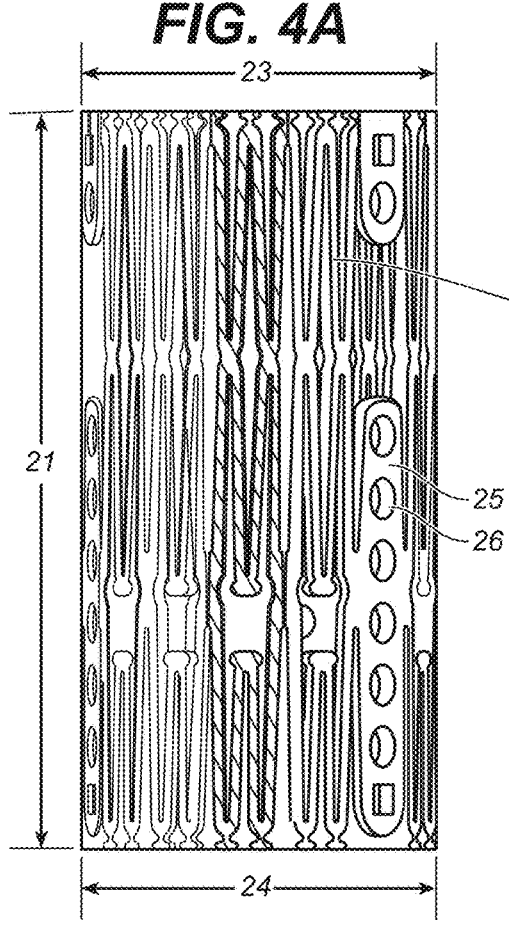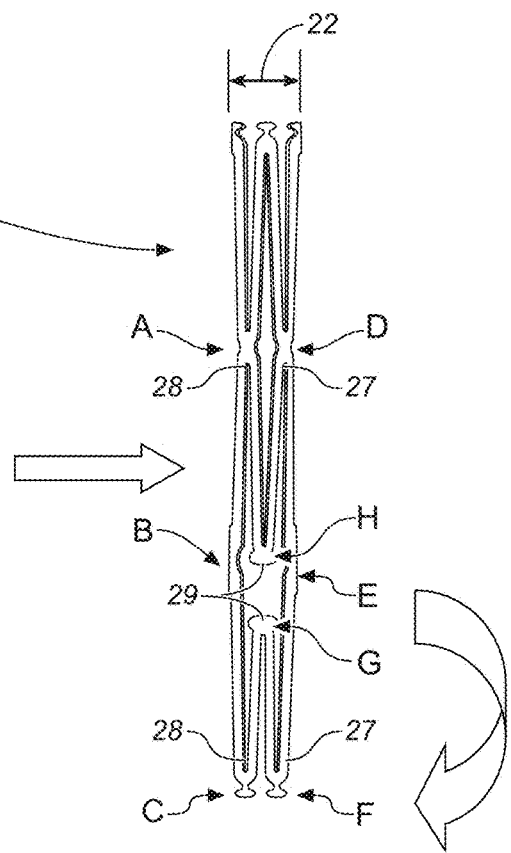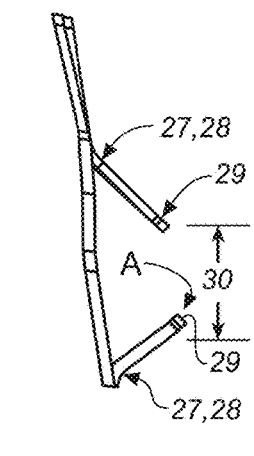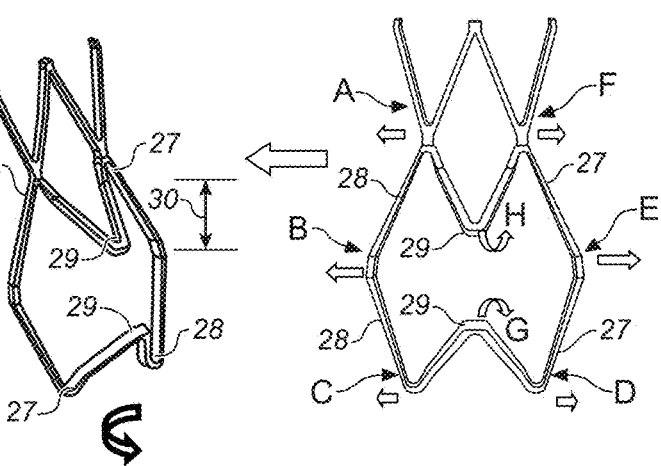
FIG. 4A  FIG. 4B  FIG. 4C  FIG. 4D  FIG. 4E

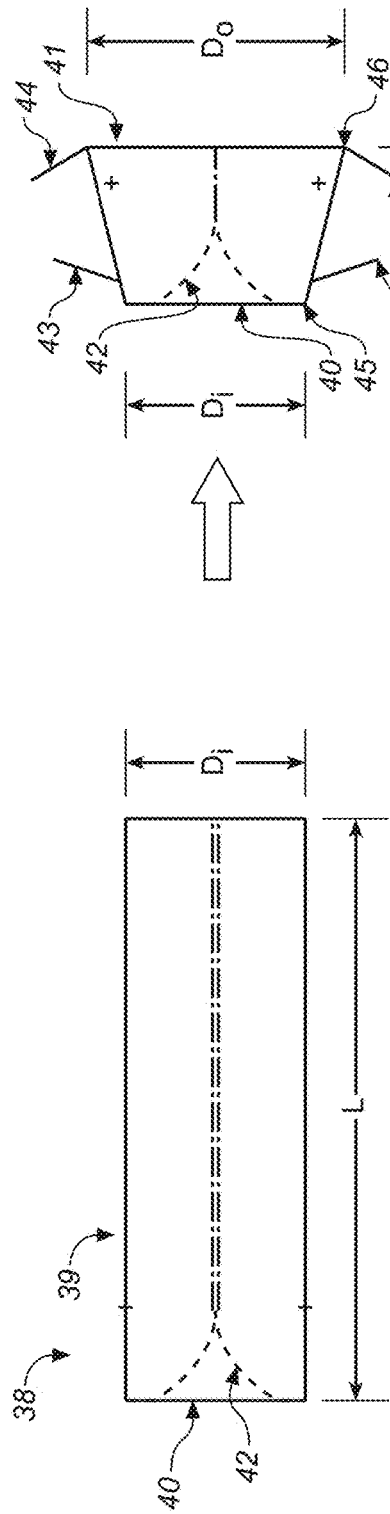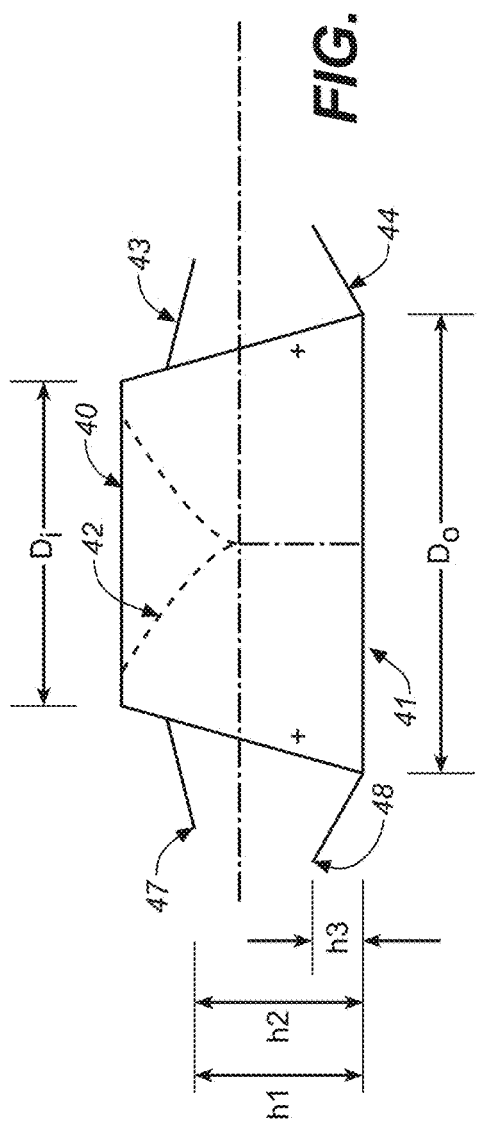

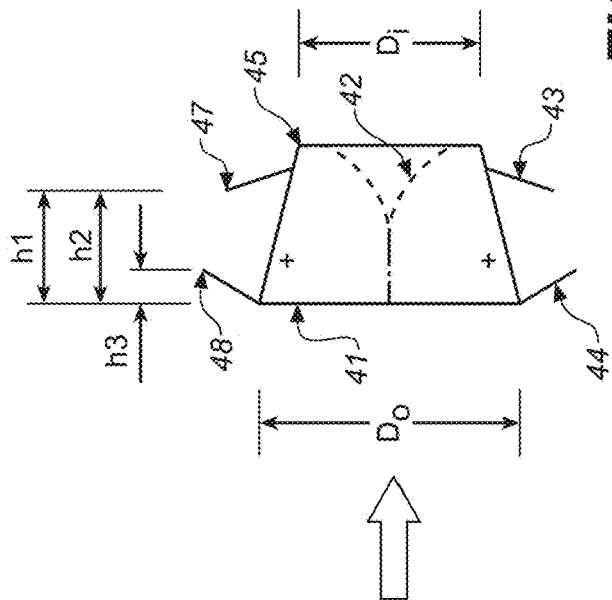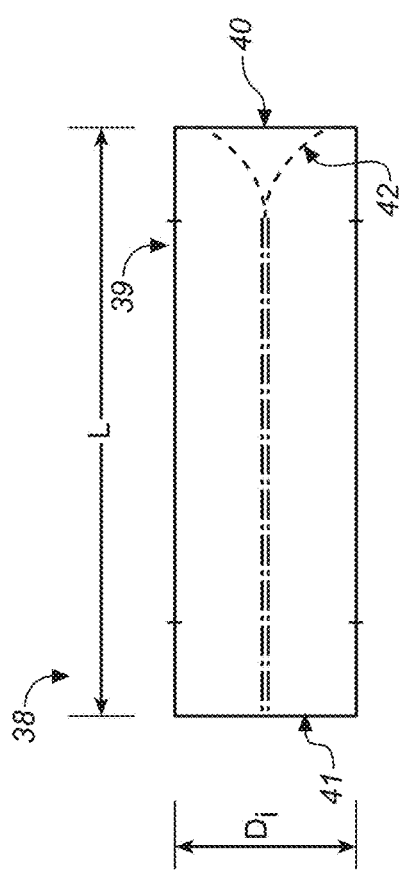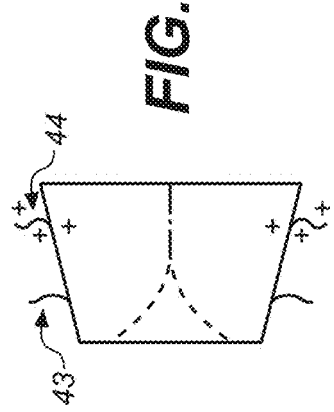
FIG. 7B
FIG. 7C
FIG. 7A

CATHETER-GUIDED REPLACEMENT VALVES APPARATUS AND METHODS

CROSS REFERENCE TO RELATED APPLICATION

This application claims the benefit of U.S. Provisional Application No. 61/802,311 filed Mar. 15, 2013, which application is incorporated herein by reference.

BACKGROUND

Each of the four heart valves in the human heart, the aortic, and mitral valves on the left side, or the pulmonary and tricuspid valves on the right side can become dysfunctional in many ways at any time. Such events including infections, structural failures such as tears or disruption of certain components as with the mitral valve chordae, or deformation because of genetic predisposition of valvular material, can disrupt the normal unidirectional flow of blood in the heart and the rest of the body often with fatal consequences. Cardiac valves perform a critical function in maintaining every tissue in the body with an adequate supply of nutrients, carried by the blood, as well as maintaining pulsatile flow through the vasculature to perfuse various organs in the body. Often when there are congenital malformations of some or all of these valves diseased at birth, an infant's life depend on quick and well-structured repair or replacement of the valves.

The development of external cardiopulmonary oxygenation with the heart lung machine made it possible to stop the heart to ease surgery to repair or replace the diseased or dysfunctional valves to save lives in spite of the trauma. The invasiveness of open chest and, open heart surgery and post-surgical complications inherent in such surgeries, also places the older population at high risk for mortality. The old and frail are often denied surgery after risk assessment and are treated instead with a range of relatively ineffective medications to make the effects of the valve disorder more bearable while patients continue an inevitable decline until death.

The use of catheter techniques to deliver and implant vascular stents in the coronary arteries to recanalize or dilate these arteries, to preserve blood flow to the heart muscle, allowed the removal of the blockage and the restoration of blood and oxygen flow to the heart muscle. Such techniques have become routine as millions of catheter-delivered stents have been placed worldwide in a relatively safe and effective manner. The techniques inspired pioneering developers in the cardiac value field to attempt to deliver heart valves in a similar manner. The technique depends on the ability to produce a frame or stent that houses a valvular mechanism, termed a valved stent, made of materials that can maintain their structure and that may be introduced through the vasculature and guided while mounted on a catheter. The valved stent is often placed within a capsule incorporated at the distal tip of the catheter to minimize damage to it and to the vessel walls during placement. When the tip is near the diseased valve, the valved stent is then allowed to emerge from the capsule on the catheter, expand by itself or with aid of balloons dilated with liquid pressure, to reach the nominal size of the device. Then the stent is deployed and deposited at the proper target site wherein the valved stent will remain and the valve will perform the intended function to replace the function of the diseased dysfunctional valve.

In addition to the vascular route, catheters containing the valved stent may be introduced into the heart in antegrade route, meaning following the flow of blood along a vessel or through the heart. Alternatively, a replacement valve may be introduced in retrograde manner, i.e. with the tip going against the flow of blood. If an aortic valved stent is introduced through the femoral artery, the catheter travels retrograde to the flow of blood, through the aorta until it reaches the diseased aortic valve where it will be deposited. An antegrade route can be found if the aortic valve is reached through the tip of the heart, by puncturing the tip, although this approach requires surgical entry through an incision between the ribs and guiding the catheter through the ventricle towards the left ventricular outflow tract that leads directly to the aortic valve. This is termed a transapical route.

This route could also be used in retrograde fashion to deposit a mitral valved stent at the mitral valve annulus between the left ventricle and left atrium, the tip containing the valved stent travels retrograde against the blood flow that is proceeding towards the aorta. However, a mitral valved stent delivered through the venous side would penetrate at the femoral vein, proceed through the vena cava to the right atrium, and pass through the wall that separates the upper chamber of the left side of the heart, the left atrium, the trans-septal route. In this approach, a puncture of the wall, also called a septum, must be made to allow the catheter tip to reach the atrium and to direct its tip to the mitral valve annular plane where the deposition of the valved stent occurs. This antegrade route is clearly a short-cut without major surgical technique, to the atrium and the dysfunctional mitral valve. The first aortic valves implanted by catheter guidance were in fact done in this manner, the catheter passed through the septum, through the mitral valve and through the chordal mass and continued to reach the aorta at the base of which one finds the diseased aortic valve and where the aortic valved stent was deposited. In the case of the mitral valve, another possible route is the transatrial route, another antegrade route that is a minimally invasive surgical technique through a relatively small incision through the chest that allows approach to the cranial or superior aspect, the roof of the left atrium, through which the valved stent bearing catheter can be introduced by following a direct path with the flow of blood to deposit the device into the dysfunctional mitral valve.

At present, the choice of technique depends on the condition of the patient and to minimize longitudinal or post intervention complications. While the catheter-guided techniques for the aortic and pulmonary valves have been used extensively, now counting over 300,000 patients, these techniques have not yet translated into well-established mitral valve replacement techniques. The obvious reason for this is the complexity of the mitral valve. The mitral apparatus consists of a continuum that begins at the walls of the heart from which papillary muscles emerge that connect to a group of tendon-like filaments termed the chordae tendineae. These structures have the appearance of parachute ropes that reach into the mitral valve leaflets' edges. The leaflets themselves are of different shapes and sizes. The anterior mitral leaflet having larger surface that connects to the atrial curtain descending from the aorta, and the posterior mitral leaflet that attaches to the outer or posterior portion of the wall of the heart. Both of these leaflets and chordal mass are contained within a not-so-continuous structure generally termed the "annulus." Approach from the atrial side or the ventricular side of the valve to its annular plane poses difficulties of navigation, not only for the approach, but for the accurate deposition of valved stents coaxially (stent lined with the central axis of the mitral valve), and the capture of the necessary leaflet and annular components to remain in place, to seal the periphery between the two chambers, and to provide the necessary function.

Open surgical replacement has been performed for hundreds of thousands cases of mitral valve dysfunction until it was realized that the valvular tissue in some disorders was still well preserved in whole or in part. Top surgeons devised procedures to repair the malfunction in open heart procedures, although only recognized centers of excellence in cardiac surgery are able to perform the complex surgery. The number of patients affected with the condition of mitral regurgitation or valve incompetence graded in terms of its severity at higher than mild (moderate) and many graded severe is very large reaching many millions worldwide. Oern S, Liddicoat J.: Emerging Opportunities for Cardiac Surgeons within Structural Heart Disease. *J Thorac and Cardiovasc Surgery:* 132: 1258-1261 (2006), authors describe the incidence of disorders of the cardiac valves in the USA population, and show that on the order of 2.3 million patients yearly have dysfunctional mitral valves in various stages, with approximately 220,000 in the severe category. Of these severe patients, only about 23% (48,000) receive the proper treatment for correction of the condition. Regrettably, a large proportion goes untreated and since the report was written over one million patients have died. Present day mitral valve repair centers can only handle a few of the afflicted.

The translation of surgical repair techniques to catheter-guided less invasive techniques began in the late 1990s in the hope of enabling mitral valve surgical repair techniques. This hope was met with many disappointments when assessing the reliability of the safety and more particularly the effectiveness of such procedures. The results in many cases are only partially satisfactory with a sizable percentage of incomplete repairs of mitral regurgitation. Although a variety of approaches have been attempted, trapping the mitral valve leaflets' central edges and apposing them centrally thus creating a double orifice (reproducing the surgical Alfieri edge-to-edge repair technique with catheters) to reduce mitral regurgitation is the most advanced. Others provide reduction of annular dilatation through the introduction of metallic wires through the coronary sinus vein to circumscribe the mitral valve annulus and reduce its size by constriction, but this also met with disappointing results. A few others purported to correct the condition by repair with minimally invasive procedures but the results are poor at best.

In various embodiments, replacement heart valves can comprise certain components that are common to most devices for replacement of heart valves. There is often a component that will act as support, the frame, usually referred to as the stent. Within this frame or stent, a valvular mechanism is enclosed, often having more flexibility in the case of the so called biological heart valves, as these valvular mechanisms are to undertake the restoration of the valvular function. These valvular mechanisms are comprised of sections of thin material (usually a biological membrane) that are movable under the action of the flow of blood. These sections that can be singular or be in a plurality of two or more sections often termed the "leaflets" or "valves." Depending on the direction of the flow of blood, these surfaces will move in the same direction, so as to open the orifice that is provided by the stent as large as possible without damage to the leaflet when blood flows from one chamber of the heart to the next or towards the outside the heart. Subsequently, as the pumping stroke of the heart is finished, blood flow reversal occurs instantaneously and pushes the leaflets in the opposite direction closing the valve and impeding retrograde blood flow or reflux, also called regurgitation. Regurgitation can greatly diminish the efficiency of the heart and is considered a serious, often life-threatening condition.

The valves used for decades as implants for the major part consisted of the same components, namely a stent generally fabricated from polymers reinforced with wire, and a leaflet mechanism. The valved stents of the "new era" of valve therapy, are in general cylindrical tubular frames of metal, cut in such manner and shape to be compressed to a very small diameter, close to the original diameter of the tube while including the tissue valvular mechanism, such that the whole valve can be threaded through the vasculature with the aid of catheters, in the smaller possible profile. These metal stents are generally made of rust-free very pure stainless steels (alloys of iron and other metals) that require a liquid filled balloon under pressure to be expanded to their final or nominal diameter. However, in their final expanded diameter, such stents are still heir to the pressures the tissue may apply and can be deformed inwardly resulting in loss of the function attempted to restor. Other metal alloys used are the so-called shape memory metals that can be compressed to the small diameters desired at specified low temperature ranges and on their own, because of their molecular composition, will expand under temperature (i.e. body temperature) to their original pre-compression nominal diameter. The stents, in effect the valves, in the "new era" of heart valve therapy are conformed to meet specified and stringent requirements to perform the needed function, specifically, the ability to remain in the target site at the native annulus without dislocating or migrating, such that the replacement valve remains anchored in place for the rest of the patient's life. Valve function is needed. In addition, the valved stent must seal the periphery to avoid leakages (some leakages are in effect regurgitation) that can be very damaging to the blood and the health of the patient, and otherwise may require revision or surgery for correction.

The use of stents in aortic valve replacement therapy is mostly for aortic stenosis, a disease that often occurs because of the pathological mineralization of the tissue that constitutes the aortic heart valve. Leaflets of the aortic valve become thickened and calcium deposits by diffusion from the blood plasma within the leaflet tissue and at times on the surface of the tissue, hardening the leaflets and their mobility to the point that they practically close by narrowing (stenosis) the orifice leading from the left ventricle to the aorta so that blood cannot follow a normal flow. The ventricle pumping overexerts its muscle which becomes thickened trying to pump blood through a smaller orifice of the aortic valve and slowly its function decays. The body is deprived of blood and organ conditions and quality of life decreases rapidly. Catheter-guided implanted valved stents that are used to correct the disease rely on purely the force exerted by the stent on the calcified rocky leaflets. These stents are cylindrical in the neighborhood of the valve and the walls of the cylinder exert the pressure that keeps the valved stent in the area of the native aortic valve. This pressure will be exerted by dilation of the stainless steel valved stent with a balloon, or by the temperature shape memory force the expanded stent can exert. It is an entirely different set of conditions that are present in the case of mitral valve regurgitation.

Mitral regurgitation (MR) can be caused by many conditions of which some are more amenable to the use of valved stents. One form that results from changes in the shape and size of the heart, by dilatation of both heart and mitral valve annulus (dilated cardiomyopathy, DCM) results in alteration of the valvular function and as such is termed "functional mitral regurgitation." It is a vicious cycle, when myocardial (heart muscle) damage results in left ventricle dilation which in turns leads to apical dislodgement of the papillary muscle, leading to annular dilatation. These two effects combine to produce mitral regurgitation causing left ventricle overload and that in turn results in left ventricle dilatation and the cycle begins again. When the annulus, the mitral valve, and the atrial curtain lose the ability to maintain the size of the mitral valve orifice, dilatation can expand this orifice to almost double its size in extreme cases. In such cases, the valve leaflets are far apart at a time in the heart cycle (systole) when they should be in apposition and closing the valve orifice to impede reflux into the chamber (atrium). The annulus is soft and somewhat pliable and exerting pressure radially as is done with the aortic stents lead to more expansion thereby aggravating the condition.

Currently, no prosthetic mitral valve devices have been fully developed and commercialized for placement in a dysfunctional mitral valve or replacement of the native mitral valve function by percutaneous means or catheter-guided means. A very strong need exists for improved designs of valved stents, and devices of delivery that will result in improved embodiments to replace the function of mitral heart valves, and tricuspid valves. These devices must enable the precise delivery, deployment, and deposition of valved stents into the atrioventricular annuli and their engagement with minimal complications and restoration of function as near as possible to that of normal healthy human valves. These devices must also prevent the development of peripheric valvular leaks (PVL), the development of leaks between the implanted valved stent and the native valular tissue, to which the valve stent must conform very closely. These conditions also require that the valve be operatively paired with a specially designed valve stent and a specially designed delivery system.

SUMMARY OF THE INVENTION

The present invention relates to medical devices and replacement heart valves, preferably those implanted by catheter-guided means. The present application relates particularly to a device with a specific geometry for both the shape-memory metal mounting frame and the biological membrane cardiac valvular mechanism to be mounted within, that enables the truncated cone geometry of the completed assembly, in one aspect a diffuser, in another an inverted diffuser, to be used as a replacement heart valve without unduly encroaching upon the atrium or upper chamber of the patients' heart, in the first case, or the subvalvular mechanism of the patients atrioventricular valve in the other. This device can be implanted into dysfunctional mitral valves of both, quadruped animals and human hearts by various means, including the threading of catheters containing the diffuser through vessels leading to the heart, that is the operator controls the delivery of the deployment shape of the diffuser at a distance from the target site for final placement of the device where the operator manipulates the apparatus to enable the device to assume the deployed shape. Alternatively, reaching the target site is also possible through direct insertion during open chest, open heart surgery or by direct passage through the apex or tip of the heart into the mitral valve area. Because of the unique design of the valve and the deployment apparatus, a series of specifically selected steps and operations or maneuvers are preformed to accomplish the final deployment and to achieve the final deployed shape and function of the device.

The invention addresses the need for new geometric designs aimed at minimizing the issues described above for valves implanted at the junction of atria and ventricles, the atrioventricular valves, the mitral valve of the left side of the heart, and the tricuspid valve on the right side of the heart, although not limited to these but also allowing their use in treating the remaining heart valves, pulmonic and aortic. With some modifications, the geometry and device may be also used to correct incompetent valves in the venous circulatory systems particularly in the upper and mostly lower limbs.

In its simplest embodiment, generally to simplify its fabrication or manufacture, when addressing the device for use in the correction of regurgitation of the mitral valve, the device here described may consist of a circular tubular structure having an entry section or orifice at one end and one exit section or orifice. This tubular structure incorporates a plurality of surfaces of specific shapes and dimensions, made of biological membranes. These surfaces are attached within the tubular structure at one of the margins along a length thereof to create a margin of attachment that joins an arc of its periphery and maintains these surfaces within the inner sector (LUMEN) or volume of the tubular structure, while allowing other margins of the membrane surfaces, their free margins, to float in the direction in the blood or liquid is flowing. While the free margins of these surfaces allows their excursion toward the inner surface of the circular or cylindrical structure, it is meant to do so under restriction a certain distance from the inner surface of the tubular structure at the end of the excursion to avoid impingement and damage to the floating surface structure. These surfaces however, when the direction of the fluid or blood reverses, will also reverse their excursion to approach adjacent free floating surfaces, at which points the surfaces are shaped and designed to the joinder region as a part of the total surface of apposition so that abutting adjacent surfaces create a closure that impedes the reversal of blood flow. Prosthesis is also comprised of a frame or stent to support the leaflet valvular mechanism.

The mitral apparatus ordinarily appears to be in the form of an inverted diffuser, a device for utilizing part of the kinetic energy of a fluid passing through a machine by gradually increasing the cross-sectional area of the channel or chamber through which it flows so as to decrease its speed and increase its pressure, wherein the diameter of the passage way of the valve may diminish slightly as blood proceeds from the atrium to the ventricle. However, in the heart, the pull on the leaflets exerted by the chordate and the papillary muscles opens the cone and expands the smaller orifice to allow blood to flow with very little pressure. Accordingly, the geometry of the tubular structure of a replacement valve may be approximated by a truncated cone. This tubular structure, while it may have uniform diameter (cylindrical) in an embodiment that eases manufacture, preferably should have different diameters at the fluid entry and exit aspects. In the case where the entry aspect exhibits the largest diameter as compared with the exit diameter, the mitral bioprosthesis of the intention is in the form of an inverted diffuser that reflects the native geometry of the mitral apparatus in the normal condition but has no way to expand the exit diameter as the native valve does. Should the converse be true, the entry diameter may have a lesser dimension than that of the exit diameter, thus the condition of a diffuser is met. The diffuser allows for dissipation of fluid pressure along the axial path.

The valved stent is placed with the smaller diameter entry aspect, the inflow aspect of the mitral valve within the upper chamber, the atrium of the heart. By having the minimal size entry diameter, the valve requires the least pressure gradient to open and close. The geometry is optimized to require the minimum height with an opening and closing (coapting) mitral valve that simultaneously exhibits the least possible protrusion into the left atrium. Given the dimensions of the left atrium in the human, and even more critical in quadrupeds commonly used as in vivo test animals, the contracting motion of the atrium would contact the entry aspect of a prosthesis with excessive vertical dimensions that intrude in the LA.

The anatomy and morphology of the papillary muscles can vary from heart to heart in both the human and animals, at times residing further from the annular plane of the mitral valve (distally), or tricuspid valve in the right side of the heart where the group of muscles may also vary in number, so that the muscles are closer to the apex of the heart. Both in the normal and pathological conditions, the muscles may be more atrially placed (cranially displaced), that is, closer to the mitral leaflets of the valves. In the latter condition, the distal ends of the valve stent would most probably impact or contact both papillary muscles and their junction to chordal masses. Thus, the tapered shape of the valve stent may be suitable for the replacement valved stent to avoid the complications from contact between the atrium and the prosthesis, including laceration, possible chordal rupture, rhythm disturbances, etc.

The diffuser is the tubular structure wherein the fluid flow will enter through a circular or close to circular (oval) entry aspect and as the fluid flows forward, the walls of the structure are found to be further from the central axis, or the tubular structure flares out linearly so that where the structure ends, the diameter or the distance of the wall to the central axis will be larger than that at the entry point. Thus, the structure of the diffuser is akin to a truncated cone with the inlet area or peripheral dimensions are smaller than those of the exit area peripheral linear dimensions. The linear flaring (not curvilinear as is the case of a trumpet flare) in this case becomes necessary to maintain uniform stresses and strains on the frame metallic structure, therefore along the flow direction or in the reverse direction the metallic stent should have uniform stresses and strains.

The stent or frame, wherein the valvular mechanism resides or is mounted is also in the same general form. Adopting this cooperating conformation allows the height dimension to be reduced without compromising the flow/pressure properties of the valve while minimizing the intrusion of the device into the left atrium. Given that a diseased mitral annulus could be enlarged 30%-50% above the normal diameter or cross section, causing the valvar leaflets inability to meet and resulting in mitral regurgitation, the "annulus" of the prosthesis should be of similar size to the dilated patient annulus so as to be able to anchor the device fully onto the dilated patient's annulus. However, the conformation does not require a valvular mechanism or a valve that can open and close normally and has the exact same dimensions as the annulus. The device does not need to be cylindrical, but the valve may be located slightly above the annulus not far enough to disrupt the normal function of the left atrium.

DESCRIPTION OF THE FIGURES

FIGS. 4A-4E show the collapsed and expanded views of the stent structure of the replacement value apparatus, including the expansion of a single element of the stent.

FIG. 4A is the collapsed configuration of the stent structure as confined into a cylindrical configuration for minimally invasive deployment. The shaded portion is an element of the start isolated and expanded in FIG. 4B-4E.

FIG. 4B is an element of the stent shown in isolation to illustrate the superior and inferior connection, and the out-of-plane expansion intermediate winglet/teeth structures upon expansion and prior to deployment of the valve stent.

FIG. 4C is a side view of a stent element following expansion showing the radial/angular extension of the winglets caused by the expansion of the stent structure.

FIG. 4D is a rotated view of FIG. 4C showing the radial extension of the intermediate, superior and inferior portions of the winglet elements.

FIG. 4E is a superficial view of an element of the stent structure showing the deployment of the eight points (A-H) identified in FIG. 4B to reveal the orientation upon expansion of individual elements of the stent structure.

FIG. 6A is a drawing of the side view of the valved stent showing the stent that holds a valvular mechanism within in the compressed cylindrical configuration.

FIG. 6B is a drawing of the side view of the valved stent showing the expanded stent configuration, that of a diffuser or truncated cone with the expanded valvular mechanism showing coaptation of the leaflets during the closed valve part of the function mechanism.

FIG. 6C is a schematic of the side view of the expanded valved stent configuration wherein the deployed positioning member surfaces have been curved to improve the tissue contact surface area interface.

FIGS. 7A, 7B and 7C are schematic drawings of one embodiment of the stent depicting the reversed loading of the valved stent so as to allow possible deployment of the stent from a retrograde delivery.

DETAILED DESCRIPTION OF THE INVENTION

Figure 1:
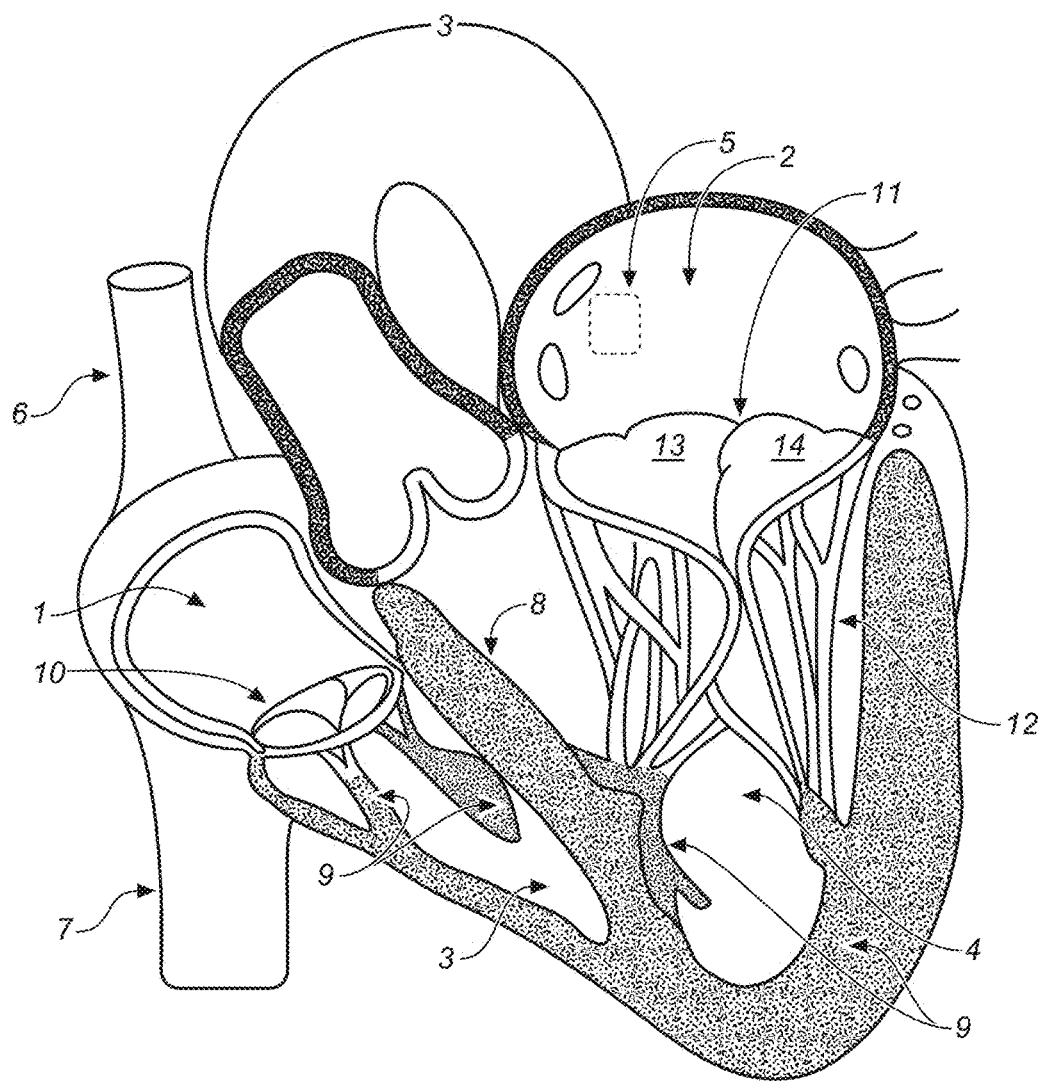
FIG. 1 shows the structure and operation of a normal heart.

The invention is a device, several component parts, specifically for delivering an artificial heart valve for replacement of a diseased or dysfunctional heart valve. The device including a stent, a stent combined with a valve described herein as a "valved stent" or "valved frame" and the delivery device described below in various designs to facilitate the implantation of a replacement valve assembly that will return function to dysfunctional atrioventricular valves and that heretofore are considered difficult to deliver, deploy and have function with minimal complications. All the inventions described are not limited to atrioventricular valves (mitral and tricuspid valves) but can be applied to replace the function of any of the other cardiac valves.

One device of the present invention comprises an expandable support member generally called a stent, and a valvar mechanism attached to the main body at the interior of the expandable support member, collectively referred to as a "valved stent." The device can be cycled from one radially contracted or collapsed configuration to one or many radially expanded configurations. The expandable support member has a first end aspect, a middle aspect, and a second end aspect and within the two end portions extends the main body. Consistent with these aspects, the main body portion includes three different outer circumferential surfaces generated by three main circumferential axes or diameters that describe a truncated cone also known as a diffuser. Both outer and inner surface of the diffuser are in the same truncated cone configuration. The device also comprises a valvar mechanism or prosthetic valve that closely fits the inner support member's surface to which it is attached by specific means. From the outer circumferential surface, the main body can generate a plurality of surfaces of various shapes or geometries by extension of part of the surface. These extensions, winglets or tines will occur at specified angles, and will have specified lengths and surfaces relative to certain dimensions of the main body, and will occur or extend in specified directions. Each winglet has end portions that are attached to the body or structure of the stent and adjacent to the main body surface in both the radially compressed and radially expanded forms. Each winglet also has an intermediate portion terminating in a tip that is not be attached to any part of the main body except through the end portions of the winglet, but will terminate suspended in space. In the radially compressed state of the device, these winglets are an integral part of the surface and are coplanar with the outer and inner surface and help to form the surface. Said winglets proceed or spring and radially extent outward from both the superior surface of the truncated cone and from the inferior aspect of the truncated cone, maintaining between their ends, the second axis or second radius of the truncated cone at a prescribed distance such that the space between their ends forms an expandable region or cavity having a defined distance to accommodate the native valve annulus and part of native leaflets.

The winglets may have a pointed tip or present a rounded configuration at the end that terminates the portion suspended in space to avoid damage to inner cardiac structures. Additionally, rounded ends are pointed away from direct perpendicular contact or impingement with the surface of any of the tissue structures in contact. In this manner, the rounded portion serves only as a contact and encompassing surface that will not impinge on the tissue surface with movement of the contact area due to the function of the heart while pumping blood. Additionally, the superior aspect winglets that will rest on the native annular surface may be covered with a biologically compatible medical fabric that itself will elicit the deposition of fibrous ingrowth of material that will increase the sealing of the stent-tissue interface and lower the thrombogenic potential of the valved stent materials.

Thus, means for a valved stent to secure the annulus and nearby leaflet tissue are comprised of materials that grasping the tissue softly but firmly to have the valved stent remain in position and prevent migration. Securing the valve stent is accomplished by providing the frame or stent with sets of tines or winglets that grasp from one chamber side of the annulus, in the ventricle and grasp the annulus at the atrium aspect of the annulus. The winglets necessarily exert a securing hold without tearing the tissue of the annulus.

The invention is capable of delivering a valved stent to fit a dilated native heart valve and anchoring the valved stent in place. The valved stent may have anchors attached to areas of the dysfunctional valve in contiguous chambers. These anchors mirror each other as they attach the stent between contiguous chambers and oppose each other in opposite directions from opposing chambers to cause a clamping of the borders of the contiguous chambers between opposing chamber winglets such that said tines restrict the stent from wholly moving into the opposing chamber, i.e. from one chamber to the contiguous chamber. The atrial anchors restrict passage of the valved stent into the ventricle, and conversely, the ventricular tines impede the passage of the valved stent into the atrium.

The geometric shape of atrial winglets, tines or anchors may yield a sealing function. One of the design limitations of some previous transcatheter valves for the aortic position that has been difficulty in overcoming peripheral or paravalvular regurgitation (occurring in about 40% of patients after catheter guided aortic valve replacement), that is, leakage of blood around the periphery of the valved stent which has been found to carry a direct relation to mortality for a significant number of aortic patients treated with transcatheter aortic valve replacement devices. With mitral valve devices designed to close the valve orifice and impede blood flow in reverse direction, toward the atrium, because of the pressures involved during the cycle of the heart, when the mitral valve closes (during systole) the heart ejects blood from the ventricle through the aorta to the rest of the body at very strong ejection velocity and pressure. Small or larger perivalvular leaks (PVL) around the periphery of the stent toward the atrium could cause extensive hemolysis (breakdown of red blood cells that have very fragile cell walls) and have untoward effects on the health of the patient and the performance of the mitral valved stent.

The superior winglets of the valved stent, when rounded and enlarged, are intended to provide good apposition of the inflow aspect of the valved stent in turn also providing a sealing function by also capturing between superior and inferior tines a good quantity of the leaflet to seal the periphery of the valved stent. The radial force of the self-expanding stent, together with the stents external inclined or tapered surface, contribute to maintain fit of the periphery of the stent in apposition with the periphery of the annular orifice created by the annulus and leaflet joints and tend to accentuate the capture of material between anchors to provide a better seal. This superior set of tines can be obtained by pivoting members arising from the surface of the stent lattice at set angles or by extension of the upper aspect border of the stent by reverse bending inferiorly at the set angle of the winglets to assume the tine shape.

These tines may be deployed sequentially, so as to promote improved anchoring such that upper tines deployed first while holding inferior or outflow tines. Allowing the upper tines to deploy first improves fitting the valved stent onto the annular plane and into the valve inter-chamber orifice thereby improving coaxial implantation (central), decreasing unnecessary intrusion of the stent into the lower chamber (ventricle) as the superior atrial aspect is restricted to remain in the atrium, and reducing canting, which is a form of dislocation and migration which will also produce leakage. Ventricular winglets can arise from the inferior or outflow border of the stent lattice, and alternatively can arise from the commissural posts broad member by pivoting radially outwardly or from additional posts between the commissural posts to maintain a plurality of posts and winglets. Extended posts from the inferior or outflow border of the stent, feature either or both a neck and an eyelet with which the aspect (outflow) could be held crimped within the capsule without expanding while allowing the alternate aspect (inflow) to expand such that a controlled deployment and release for implantation can be made by the operator.

In the normal human being the mitral valve is close to an ellipse in shape and generally its nominal size is given as the size of one of its axes, the commissure to commissure axis (C-C), although the anterior-posterior (A-P) axis changes slightly from that during systole when it becomes more elliptical, ranging in the normal patient usually between 80%-90% of the C-C axis; thus, the eccentricity of the mitral orifice (or annulus) that in the patient presenting with MR becomes practically oval is in the order of 0.85+0.05. Some show it to be D shaped. To ease the choice of prosthetic valve replacement, it is approximated to be circular since introduction of a larger valve would stretch one axis while reduce the other to approximate a circular shape then the replacement valve mechanism may be circular with three leaflets that will provide the function. The normal mitral valve is then sized as between 25 mm in diameter for small bodied person to 33 mm in a large hearted person. The abnormal condition (MR) with an annulus that dilates to more than 150% of its normal size results in a very dilated incompetent mitral valve with diameters ranging from the middle 30s mm to in extreme cases slightly larger than 50 mm. This introduces another substantial difference from aortic therapy when a percutaneous approach is done, since a larger than 40 mm diameter valve must be reduced to a small compressed profile to load into a catheter to thread through normal vasculature and is difficult for because such a compressed diameter is significantly larger than the compressed aortic valved stent that is already almost at the limit of the acceptable size of passage for most human or animal vessels.

More importantly, the valved stents have generally been designed from cylindrical metal tubes and when expanded result in cylindrical stents. In such geometry, the valved stent has also a cylindrical configuration, meaning that when expanded, the radius throughout the length of the tube or valved stent is uniform. In the MR patient, the dilated annulus to 40 or 50 mm then would have to have in the extreme 50 mm cylinder to close the passage from the atrial to the ventricular side of the left heart. Consequently, the valve in such a stent will have a plurality of very large leaflets making a 50 mm diameter valve that can be equated to having enormous sails to close the valve, and that such large surface by Pascal's law must sustain on a per unit area the force generated by the blood when forcefully closing the mitral valve to eject blood through the aorta to every part of the body. That force per unit area is the instantaneous pressure generated by the ventricle, also known as the dp/dt, the differential pressure over the fraction of a second that causes the closure. This pressure is in the order of 2000 mm Hg/sec when at rest in the normal human, and increases to many thousands with exercise. The patient presenting with MR can only generate lower dp/dt because flow is directed both in aortic and left atrial direction, thus weakened, the dp/dt is still on the order of ca. 700-900 mmHg/sec which is significant enough to displace a valved stent from its anchored position particularly since dp/dt would return to higher values once the incompetence valve has been replaced. Such force has been known to quickly damage leaflets of native, artificial mechanical or biological tissue mitral replacement valves. Being proportional to the area presented by the leaflets, the size of the leaflets that receive the impact [Pascal's Law] is reduced by the inflow aspect of the tubular structure of the valved stent. Also, the grasping mechanism is fashioned from metal stents in a traumatic or rounded form as possible. Accordingly, the annulus engaging winglets are preferably a surface rather than a true point or tine to avoid impinging vertically into the tissue (leaflets and annulus). The mitral position does not require a valve larger than 30 mm in diameter to maintain a transvalvular gradient (difference in pressure between atrium and ventricle) no greater than 5 mm Hg to drive blood flow across the chambers. Thus, the geometry of the stent is not preferentially cylindrical but a diffuser or a truncated cone, with a lower diameter on the atrial side and the large diameter at the outflow to capture the dilated annulus on the ventricular side. Although a curvilinear flare is feasible, a truncated linear cone is used in most applications. The structure three distinct diameters: a first diameter at entrance of blood into the valved stent, the atrial side diameter, being the smallest diameter; a second diameter downstream of the first, rather a band bordered by two close diameters that represents the region that will be encompassed by a plurality of anchors opposing each other from superior and inferior aspects of the valved stent, or the space wherein the dilated annulus of said mitral apparatus will be captured and therein causing a sealing of the border between the contiguous chambers, the atrium and the ventricle; and, a third diameter successively larger than the second diameters that will expand to a dimension slightly larger than the dilated mitral valve annulus and thus impede the possibility of the closed valved stent being ejected from its landing position towards the atrium when the dp/dt exerts its maximum pressure. In some embodiments, both atrial tines and ventricular tines share the same configuration because of the inclined surface of the upper or atrial side tines would necessarily be larger if both are to meet at the same distance from the central axis of the stent to anchor the valved stent in place.

The plurality of "tines" immediately below and surrounding the atrial aspect of the valved stent, consists of extensions that are purposely larger and self-expand away from the truncated cone surface, and are shaped as flower petals to create a circular area larger than the dilated annulus to impede the passing of the entire valved stent in the direction of the ventricle thus having both the functions of antimigration and creating a wide sealing area to prevent peripheral or perivalvular leaks of blood in either direction. Altogether, the embodiment of the valved stent in the form of a diffuser or truncated cone, serves also to maintain a low height of the stent, as height can be important in some patients with a low atrial ceiling, and is contraindicated when performing safety and performance studies in quadrupeds human clinical trials models whose atria have very low ceilings. Height is also an extremely important factor in maintaining proper hemodynamics, as the blood arriving into the atrium from the lungs through the pulmonary veins (superior and inferior veins) would become turbulent and lead to thrombus formation at the low pressures of that chamber, since a valved stent protruding highly into the atrium would cause the blood to pool around it and seek motion upwards to be able to enter the upper orifice of the valved stent near the atrial ceiling. Additionally, the atrium has contractions, although not as pronounced as the ventricle, but enough to present the possibility of contact of the inner lining or surface of the atrium with the valved stent frame that in turn leads to possibility of tears, lacerations and in the minimum rhythm disturbances as the electric signals for the beating heart are conducted on the surface of the inner atria. These rhythm disturbances present as atrial fibrillation, an abnormality in the rhythm and speed of heart contraction and relaxation that can lead to death.

Notwithstanding the change in diameter, the stent itself is cut from a cylindrical metal alloy tube that self expands to the pre-determined geometry described herein as a diffuser, or the truncated cone, with a plurality of leaflets preferably of chemically treated biological tissue, configured to allow opening in one direction to maintain unidirectional blood flow when implanted, but when compressed to be inserted in the catheter will assume once again the cylindrical tubular form ab initio. The valved stent includes extensions of main posts that feature eyelets or constrictions of the posts where the whole stent is held and controlled in place by the delivery device prior to expansion, during expansion, and upon deployment and fixation by allowing the release of the valve stent under operator control at the time of expansion at the target site.

The delivery of the valve to the target site is performed in by any different avenue wherein a tubular cylindrical sheath or capsule, enclosing the compressed valved stent and having a sheath attached at distal end of a long shaft of flexible sheath or catheter that is connected to a container or mechanism that can direct the motion of the distal end of the catheter to various angles in space. The inner sheath or capsule is configured to contain the valved stent in its radially cylindrically compressed state. The entire inner distal capsule or sheath may be contained within another distal sheath. One or both of these sheaths may be wholly movable along the central axis of both sheaths and the long catheter in either direction in a sliding manner to provide means to direct the inner capsule and its contents to the target site of the valved stent, including the area defined by both the upper and lower tines of the valved stent. The distal end of the capsule holds the outflow slotted and necked portions of the plurality of posts that sustain the members of the lattice of the valved stent, so that the larger outflow diameter is held at its compressed diameter while the upper or smaller flower-like aspect is allowed to expand radially close to its final diameter. Once that is allowed to happen and the axial introduction of the valved stent has begun and the upper tines are contacting the annular plane of the mitral valve, the ventricular tines can be deployed and allow the capture of the leaflet joints from the ventricular side such that the annulus and leaflet joints form a circular band and can be captured between upper and lower tines thus completing capture at the target site.

Accordingly, the ideal mitral valved stent device is designed that will combine a complementary stent and valve mechanism to accomplish both the accurate placement and proper fixation of the disclosed valve stent combination at the target site. The mitral valved stent device of the invention is formed from an inseparable part or complement of the mitral valved stent (MVS) and delivery system.

The heart valve assembly of particular geometric configuration has an external wall structure that is geometrically a tubular structure having an entry orifice end and an exit orifice at opposite extreme ends that may differ in dimension and shape such that the periphery of one may be smaller than the periphery of the other. The tubular structure has an annular region situated between the two orifices such that the region can match approximately the annular points of engagement of the bioprosthesis about the engaging annular region of the human or animal valve. The annular region is expandable on its own or may be expanded by mechanical means to engage the target site at the human or animal valve annulus.

The annular region is comprised of a plurality of single elements of the stent and is bound superiorly by anchoring winglets that preferably under the influence of specific temperature, deploy and expand radially and in an angular fashion away from the external surface of the structure and in an inferior direction to anchor the superior aspect of the annular plane. The annular region of the structure is also bound inferiorly by similar anchoring winglets that deploy and expand in angular fashion from the external surface of the structure in superior direction to anchor the inferior aspect of the animal or human atrioventricular valve annulus. The superior and inferior teeth or winglets impede movement or migration of the structure or valved stent in the forward or reverse direction and provide secure anchoring of the device to said annular plane.

The inner structure of the stent is covered in its interior surface with an artificial polymer material, preferably woven or knitted polyester, or polytetrafluoroethylene (PTFE), that is tightly attached by specific suturing pattern to the member struts that form the lattice of the structure of the metallic stent. The polymer backing must be sutured with tension to provide a very tight window pane-like surface that is also sutured to the tissue membrane and prevents the membrane from ballooning through the lattice under the force per unit area that the ventricle dp/dt generates with every ventricular contraction.

The present invention also includes methods for the replacement of a dysfunctional mitral heart valve. First, a device is provided said device comprising an expandable support stent member that incorporates within its main body portion a valvar mechanism that when the expandable support member is in the fully expanded configuration will function as the native heart valve would function. The expandable support member presents exteriorly varying surface from one end of the support member to a second end of the support member. Extending from the external surface of the expandable support member superior to the second radius, the member includes a plurality of petals, winglets or tines that are spaced apart from each other around the circumference and extend such that their ends attached to the superior surface of the main body will be superior to the end that extends into space, thus forming an angle that maintains the free end heading inferiorly. These superior winglets extend to a wider circumferential area than that presented by the inflow aspect of the native mitral annulus and as such will serve to maintain the inflow aspect of the valved stent slightly above the native mitral annulus and to ensure that the rest of the valved stent enters in coaxially, along the central axis of the mitral apparatus into the apparatus itself.

Extending from the external surface of the expandable support member inferior to the second radius, the member includes a plurality of winglets that are spaced apart from each other around the circumference and extend such that their ends attached to the inferior surface of the main body will be inferior to the end that extends into space, thus forming an angle that maintains the free end heading superiorly. Thus, a torus or annulus band bordered by the external surface of the expandable support member and circumscribed by the free ends of the superior and inferior winglets corresponds to the annulus of the dysfunctional native mitral valve. In a second step, the expandable diffuser-like or truncated cone shaped valved stent support member containing the valvular mechanism is radially collapsed to a cylindrical shape and inserted into a capsule of a delivery device where it is locked and held. The capsule contains the collapsed valved stent, and is then attached to the distal end of a catheter for delivery. The delivery catheter will be advanced from some entry point through the skin through a vessel that will guide to the region of the dysfunctional mitral heart valve. When at the target site of the mitral valve annulus, the device is deployed in a partially radially expanded configuration, so that the second end aspect of the expandable support member is held partially collapsed while the first end of the expandable support member is allowed to expand close to its fully radially expanded configuration. The valved stent assumes a conformation that guides the superior aspect of the mitral valve annulus such that the upper winglets rest on the superior area of the mitral valve annulus and the winglets' extension prevents the superior end of the expandable valved stent from proceeding through the orifice of the mitral valve. The inferior aspect of the expandable support member is then released and the inferior free end of winglets is deployed and extend radially to contact the dysfunctional valve leaflets below the annulus of the mitral valve in such a way that the annulus and the leaflet cardiac tissue is trapped between the winglets. This configuration creates the fiscal step of anchoring the valved stent in place to function with the normal flow of blood of the cardiac cycle.

Referring to FIG. 1, the normal healthy human heart is depicted in cross section. The heart consists of four chambers, two upper blood receiving chambers the atria 1 and 2 and two lower pumping chambers, ventricles 3 and 4. The right atrium 1 and left atrium 2 are separated by a wall termed the interatrial septum 5 and in the normal adult the two do not communicate. The right atrium receives deoxygenated blood from the superior vena cava SVC 6 and inferior vena cava IVC 7 during ventricular systole and delivers blood to the ventricle during ventricular diastole. The left atrium receives oxygenated blood from the lungs through the pulmonary veins 8 during ventricular systole and delivers oxygenated blood to the ventricle during ventricular diastole. The ventricles the two lower pumping chambers of the heart, RV 4 and LV 5 are separated by the ventricular septum 9. The ventricles are surrounded by myocardium (muscle) used for pumping, the LV myocardium being thicker than the RV myocardium since the former has to pump blood through the aorta to the rest of the body. The papillary muscles 9 of both ventricles form part of the myocardium and are attached to the atrioventricular valves, the tricuspid valve 10 and the mitral valve 11 leaflets by the chorda tendineae 12, strong fibrous cords that originate from said papillary muscles.

Figure 2:
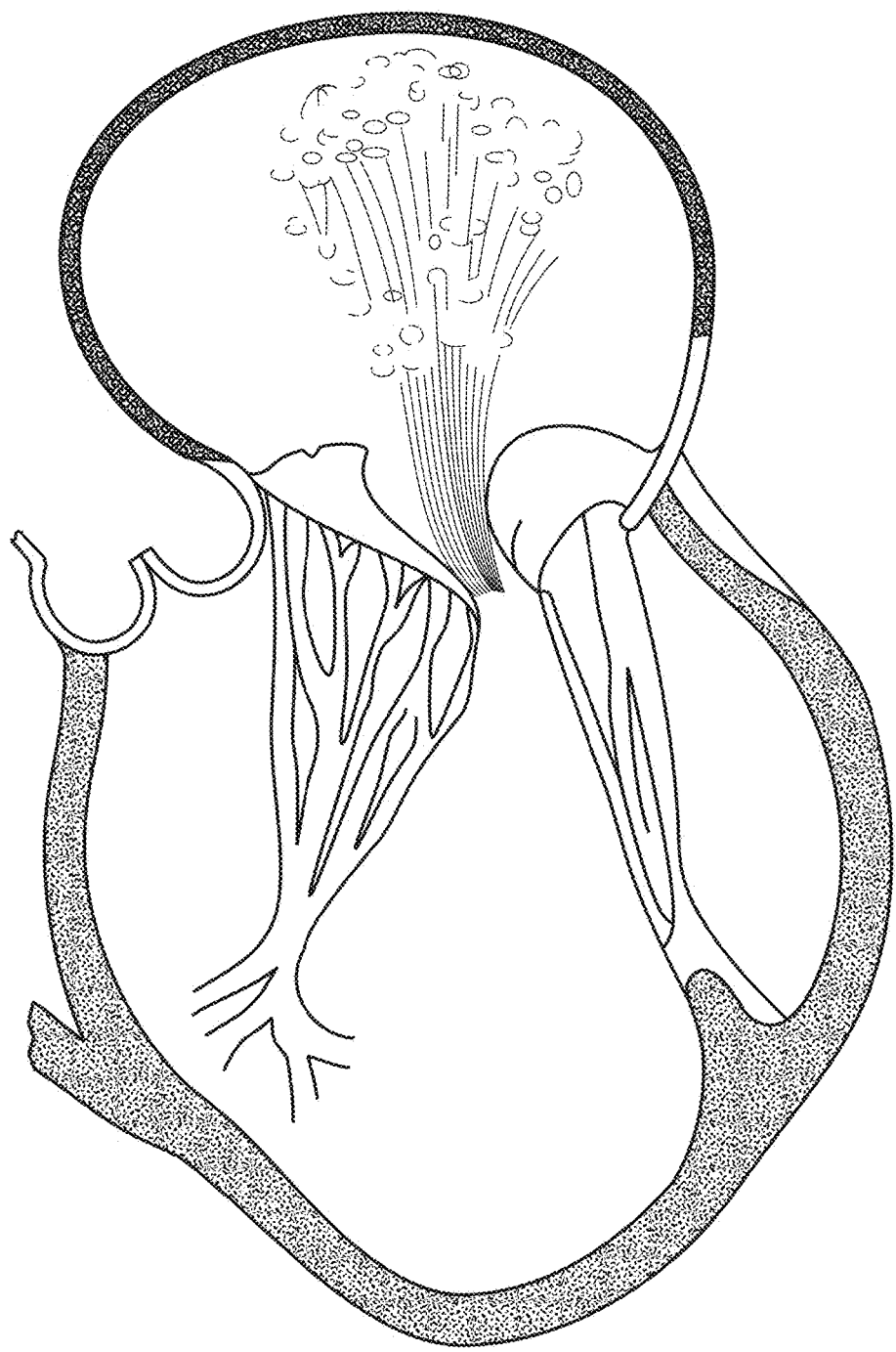
FIG. 2 shows an incompetent mitral valve with regurgitation due to a dilated mitral valve annulus that impedes leaflet coapposition otherwise known as coaptation.
Figure 3:
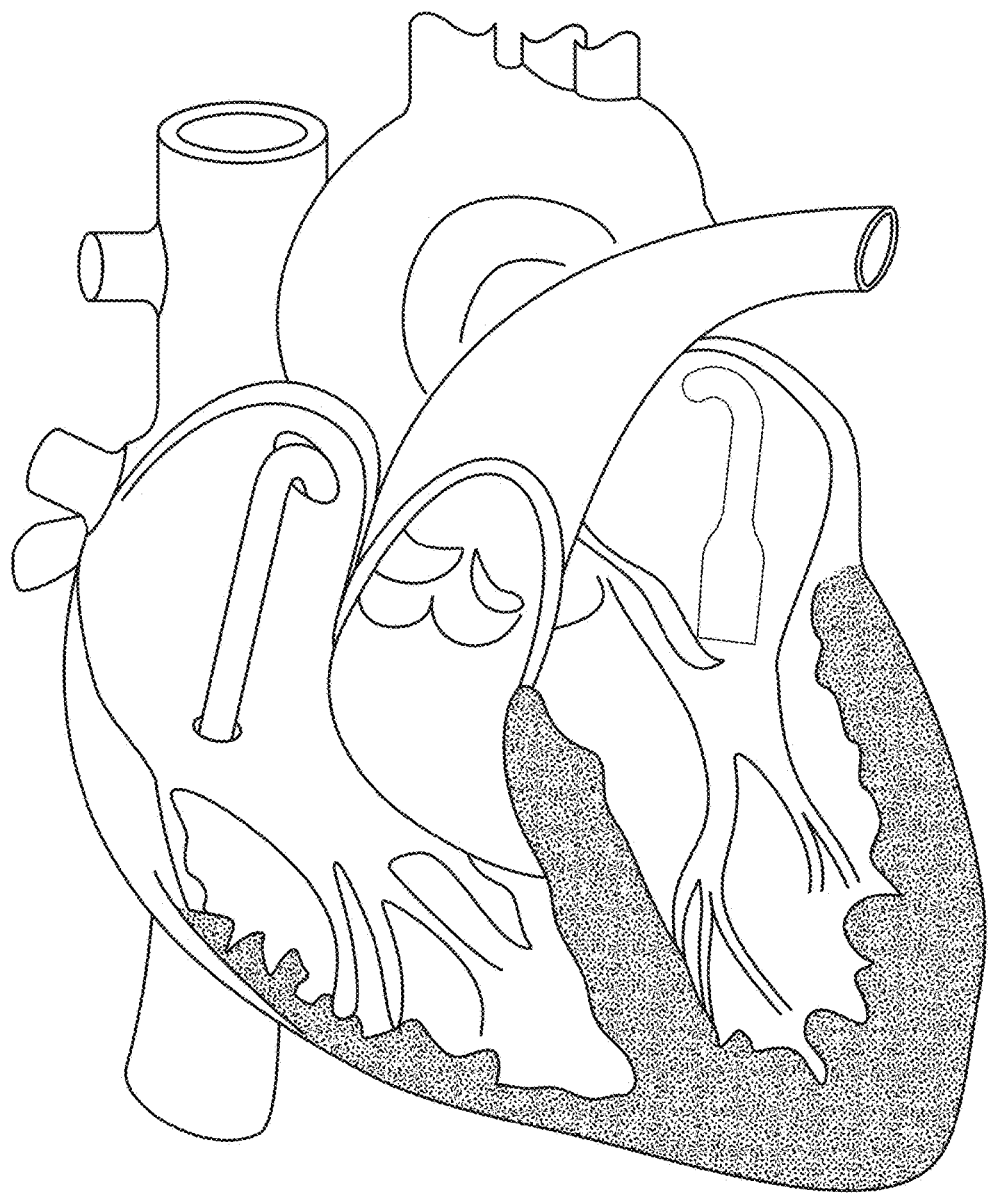
FIG. 3 shows the placement of a prosthetic valve of the invention replacing the native valve, via a minimally invasive, catheter-based placement technique.

The mitral valve 11 is in effect a continuum or apparatus that begins at the myocardium from where the papillary muscles originate and continue through the chordal mass to the leaflets, anterior mitral leaflet 13 and posterior mitral leaflet 14 which themselves continue to hinges or joints 15 and 16 that attach the leaflets at the annulus 16 and a partial fibrous and muscular region of the atrium 1 and ventricle 4. The orifice made by the normal mitral valve during diastole is shown as the ventricle relaxes during diastole and admits the oxygenated blood from the left atrium 2 shows the large anterior 13 and narrower but longer posterior mitral leaflet 14 both pulled into the ventricle. During systole when the mitral valve 11 is operating properly, parts of the anterior and posterior leaflets forceably engage each other and form a one way valve that closes and prevents regurgitaton to the atrium. Because of the action of the chordae and contraction of the ventricle 4 the valve 11 has a shorter anterior-posterior diameter and looks less circular than when open. Both atrium 1 and ventricle contract and competent flow through the mitral valve 11 play very important roles in the function of the mitral valve 11. During diastole, ventricular relaxation expands the ventricle chamber 5 forces the traction by the chordae tendineae and the flow of fast blood coming from the atrium 1 through to separate the leaflets and the 11 valve opens. Immediately, after the valve 11 is open completely, the flow through the valve 11 is reduced and at the end of diastole as the atrium 1 is contracting the flow through the valve has completed and systole the ventricle 4 contracts the papillary muscles also contract to prevent the leaflets from prolapsing or folding over each other into the atrium 2 but making the leaflets billow and oppose each other to close the orifice. The orifice is practically circular when open and will be much larger when functional mitral regurgitation occurs due to progressive dilatation of the ventricle 4 in the presence of a normal mitral valve 11 apparatus. The ventricular dilatation leads to a cycle of volume overload within the already dilated left ventricle 4, increased ventricular wall tension, and loss of coaptation of the mitral leaflets. Often the papillary muscle separation widens producing leaflet tethering and decreased leaflet closing forces all combine to result in loss of the zone of coaptation and the central jet of mitral regurgitation as shown in FIG. 2.

Referring to FIG. 4A, the collapsed configuration of the stent structure 21 is made up of 6 to 24 of the individual elements 22 shown in FIG. 4B. In this configuration, the inflow or entry aspect 23 is a fraction (i.e., less than 1) of the outflow exit periphery aspect diameter 24 such that the overall dimension of the fluid flow pathway is narrowed and tapered from the smaller opening to the larger opening. In the embodiment of FIG. 4A, the relative sizes of the entry aspect 23 and exit aspect 24 are not apparent when the structure is in the collapsed shape, but assume a predetermined relative diameter upon expansion. Additionally, the relative distance from the entry aspect 23 or exit aspect 24 are distanced at a predetermined value from the peripheral winglet structures (see FIGS. 5A and 8 below) such that the distance from both the entry aspect 23 and the exit aspect 24 are fixed relative to the native annulus. The bars 25 are also oriented in close conformity with the outer circumferential aspect of the stent structure so that the device can assume a minimum diameter profile upon placement inside a holder or delivery device. The vertical orientation of perforations) 6 are also oriented for specific engagement with the holder device. As noted above, the bars may also feature eyelets (not shown) to facilitate attachment to the holder and for manipulation during deployment.

Referring to FIG. 4B, six points designated A, B, C, D, E, and F, can be designated as relative positioning points to reveal the orientation of expansion of each individual element of the stent structure 1. Elements G and H form the winglet members and are comprised of a first and second end portion 27, 28, connected to the body of the stent member to form a pivot. The tip 29 of each winglet is not directly connected to the structure of the stent member 21 so that the tips 29 can pivot away from outer circumferential axis of the stent structure upon expansion.

Referring to FIG. 4C, the winglets extend away from the body of the stent structure but are affixed at their first and second end portions 27, 28 so that their tips 29 can engage the tissue at the native annulus. As it is apparent from FIGS. 4B, 4C and 4D, it is only points G and H that deflect out of the plane of the individual member about the circumferential axis of the overall stent structure. The angular displacement of the winglets forms a gap there between, designated A-A in FIG. 4C that forms the portion of the stent device 21 that engages the target site at the native annulus. As described in further detail below, the unique deployment methods of the device of the present invention allow a controlled expansion of the stent member 21 such that the angular displacement of the winglets away from the outer circumferential surface of the stent structure 21 is carefully controlled and allows the operator, cardiologist, or surgeon or surgeon to control the expansion of the valve apparatus to conformally engage the native valve annulus. As noted by the arrows in FIG. 4E, eight separate points on each element alter their respective conformation upon deployment to yield the structures shown in FIGS. 4C through 4E.

Referring to FIG. 4C, a side view shows the engaging winglets or teeth formed by the individual elements 22 of the stent structure 21. The stent structure or scaffold itself is formed of Nitinol or any other self-expanding temperature memory metal (preferably expanding at body temperature at or above 25 degrees C.). Circumferential displacement of the stent element with angular displacement of the winglets or teeth form tips that are formed at the outermost portion of the winglets extending from the intermediate portion of the stent structure. As noted above, this configuration causes engagement by the exterior of the stent structure both above (atrial side) and below (ventricular side) at the annulus of the native heart valve.

As shown in FIG. 4D, the lower or inferior portion winglet and the intermediate winglet extend angularly radially outward to engage the annulus of the native heart both from the atrial and the ventricular direction or orientation upon deployment. As shown in FIGS. 4B and 4E, the eight individual points (A-K) on the stent structure illustrated in FIG. 4B are displaced relative from one another but only two points, G and H as indicated by the curved arrows, are displaced angularly away from the plane of the remaining points (A-F). This is most easily seen in FIG. 4C where the points 29 of the winglets 30 are extended furthermost away from the remaining points (A-F) that remain in the plane of an element of the body of the individual element 22 of the stent structure 1. When assembled the radial extension is in all directions circumferentially about the device are shown in FIG. 5A.

Figure 5A:
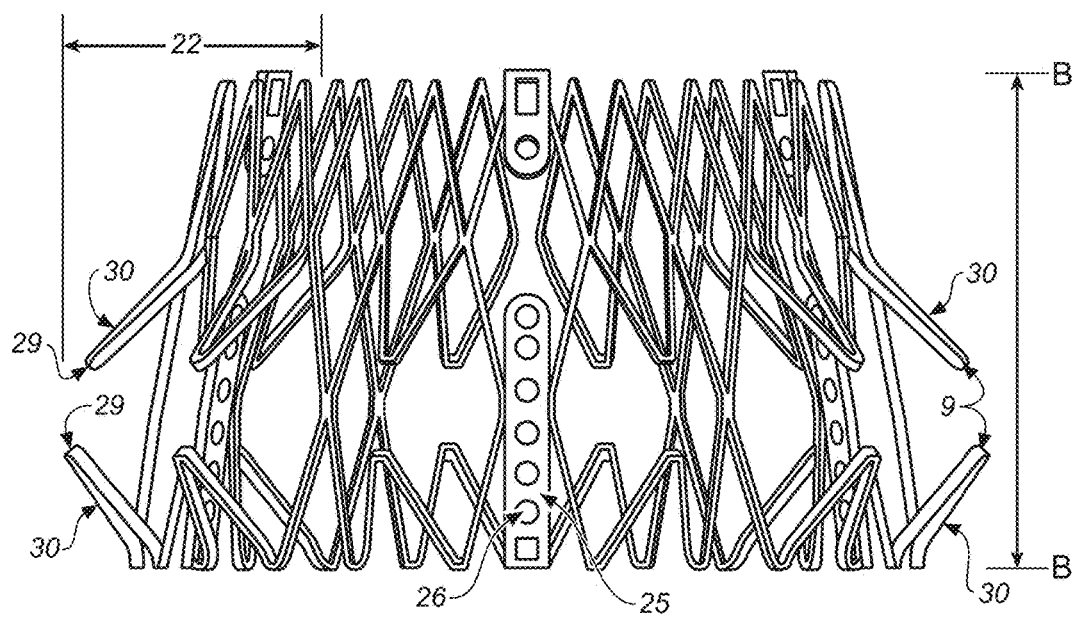
FIG. 5A is the expanded stent showing the radial extension of the intermediate and inferior lower portions forming the teeth or winglets as deployed radially or angularly away from the body of the stent to engage the mitral value annulus.
Figure 5B:
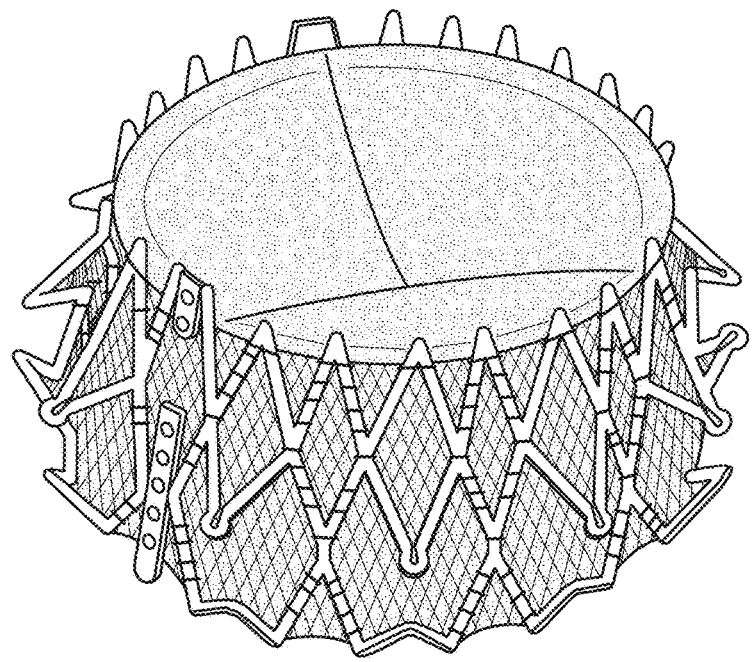
FIG. 5B is the completely assembled valve structure showing the vertical bars and the three leaflets as assembled.
Figure 5C:
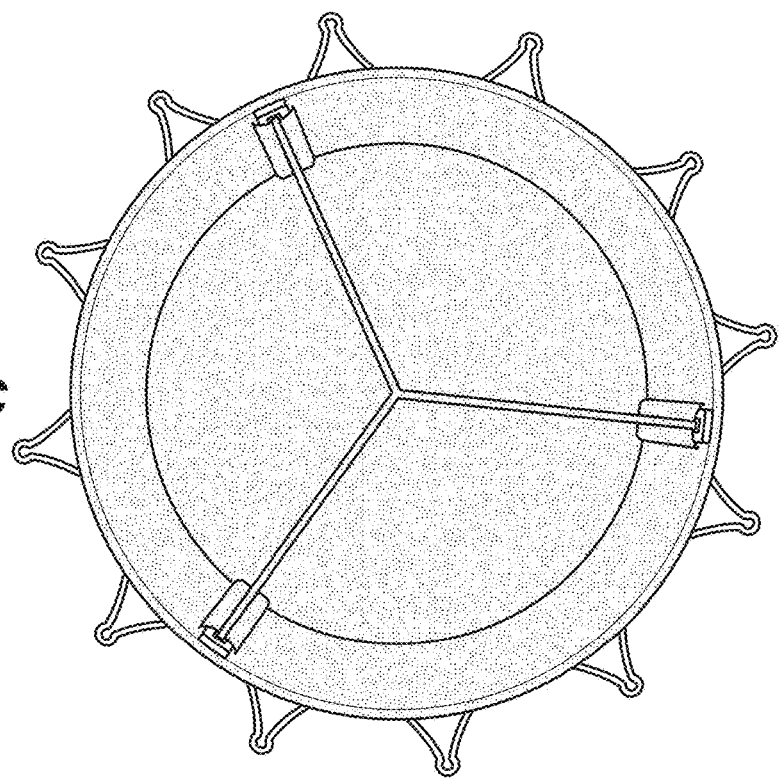
FIG. 5C is the completed valve assembly showing the three leaflet coaptation from the ventricular side and securing clips at the circumferential joining points of the valve leaflets.

Referring to FIGS. 5A-5C, adopting the form of a diffuser allows the height dimension (B-B) to be reduced without compromising the flow/pressure properties of the valve while minimizing the intrusion of the device into the left atrium of the patient. As noted above, given that a diseased mitral annulus could be enlarged 30% to 50% above the normal diameter or cross section, causing the leaflets to be unable to meet and resulting in mitral regurgitation, the "annulus" of the prosthesis should be of similar size to the dilated patient annulus to be able to anchor the device fully onto the target site at the patient's annulus. In its contracted state, the mitral valve stent has been forced to adopt the form of a cylindrical tube. FIGS. 5B and 5C shows exterior and interior views respectively of the stent component of the replacement valve of the present invention showing the stent scaffold or structure affixed to a microwoven polymer fabric (PTFE) of a type ordinarily used for implanted devices, i.e. that is biocompatible, non-reactive and non-immunogenic. The fabric material is attached to the interior of the stent structure at a plurality of points but particularly along the strut members. The specific structure of the tent scaffold is described in respect to FIGS. 4A and 5A. A portion of the stent structural member is comprised of ribbed bars extending above and below beyond the innermost edge of the entry (inflow) and (outflow) exit aspect and may form attachment points for the stent structure. The material assists in isolating the stent structure from the forces imposed by contraction of the left ventricle and the fluid flow through the interior of the replacement mitral valve when implanted. As can be seen from the replacement valve showing the stent structure in the deployed state, the intermediate portions of the stent structure are comprised of structures that deflect angularly to form winglets (teeth) at the inferior (lower) circumference in the embodiment of FIGS. 5B and 5C. In this embodiment, the outflow aspect is the larger diameter and the winglets extend radially and angularly away from the fabric to engage the native annulus of the heart about the periphery thereof. In a different embodiment, the winglets that are preferably arrayed around the entire outer circumferential axis of the device can be located at the region of the stent structure having the smaller diameter, whether that be the inflow or outflow aspect. The stent structure in FIGS. 2A and 2B ribbed bars that contain perforations for engaging corresponding devices on an introducer apparatus. The extended bars may also feature eyelets as shown in particular in FIG. 5 that also facilitate attachment to a holder. Preferably the eyelets extend at several points around the angular portion of the stent structure to enable multiple attachment points. Although the number of eyelets is not fixed, the number should be at least four to six to allow engagement at multiple points around the angular portion of the stent structure and maintain the circularity of the inflow or outflow aspect where the eyeleted members held are located.

The basic embodiment of the valved stent 38 of the present invention can be depicted in FIG. 6 as related to said valved stent as replacement prosthesis for diseased or dysfunctional mitral valves particularly those in the condition that produces mitral regurgitation [MR]. The stent of said valved stent 38 in the compressed configuration will be an expandable cylindrical form 39 shown in exemplary form in side view in FIG. 6A in which it will be until the instant previous to its final delivery configuration also shown in side view in FIG. 6B of its deployed configuration. In the compressed configuration said valved stent has a first end 40 and a last end 21 and in this configuration both first end and second end diameters are of same dimension as it is a cylinder. Said valved stent when deployed will present a first or proximal end of one diameter $D_i$ the inflow diameter that corresponds to 40 that will be smaller than a second end 41 of a larger diameter $D_o$ the outflow diameter. Said larger diameter will extend into the ventricle immediately below the annulus when deployed and expand to dimension larger than said annulus to fit immediately below the enlarged annulus of a mitral valve. The valved stent will remain in the region between the left atrium and the left ventricle without excessively protruding or overly extending in either of those heart chambers. Valved stent includes a stent, frame or support 39, a valvar mechanism 42 attached within the frame or valve support or stent and a plurality of valved stent positioning supports or anchors 43 and 44 of specific lengths and surface disposed on the surface of the stent and coplanar with the stent surface. These positioning elements can pivot about attachment points 45 and 46 such pivoting points disposed differently, the proximal pivoting point 45, that of the proximal surface or inflow anchor being distal to the proximal or inflow end of the stent 39 and the distal pivoting point 46, that of the distal pivoting surface or anchor surface located proximal to the distal or second end of the stent. In such manner when the positioning elements extend from the stent surface the distal end 47 of the proximal anchor 43 will be distal to the proximal pivoting point 45, and the proximal end 48 of the distal surface 44, will be proximal to its distal pivoting point 46 as shown in FIG. 6B. The proximal positioning element end or surface tip 47, extends radially from its distal end and conversely the distal positioning element extends radially from its proximal end. The positioning elements pivot from the stent surface at specified angles less than 90° from the surface such that the free ends of the pivoting surfaces oppose each other without touching, rather forming a gap 48 in between their ends that will present a cavity 49 where native tissue can lodge, accumulate or be grasped. Both of the pivoting surfaces or anchors may rotate at an angle equal for both pivoting surfaces. In alternative embodiments the angles formed by one pivoting surface may be different than that of the opposing pivoting surface, the angle is a minimum of 45 degrees and a maximum of up to 100 degrees without harm. When released from the capsule at a prescribed position within the mitral apparatus, the positioning elements will extend and trap within the gap formed by the two positioning surfaces or anchors 43, 44, the mitral annulus plane and the leaflet joints or hinges as the distal end of the stent 38 expands to its full diameter so that the expanded valvular mechanism 40 within the stent 39 expands to its natural configuration and the bioprosthetic valve is ready to begin function as blood within the heart continues the normal directions during its cycle.

In an alternative embodiment of the valved stent, the supporting stent's deployed positioning surfaces are shown in FIG. 6C as curved shaped surfaces, such that these gripping tines will present more of a wide surface and less sharpness at the suspended ends 47 and 48 of the tines formed by two vicinal beams of the stent lattice, the roundness and curvature to minimize the possible injurious attributes of pointed surfaces. The gap between the tines is preserved to capture the necessary leaflet joint and mitral annulus to hold the stent in place and provide interchamber sealing.

The valved stent 38 may also have the valvar mechanism oriented in a reversed manner as shown in FIG. 6B, such that the inflow aspect or diameter will be allowed when deployed to open partially or fully to its terminal diameter while holding the outflow diameter to the original cylindrical diameter of the crimped configuration.

FIG. 7A and FIG. 7B, show the side view of the compressed cylindrical valved stent 39 with stent 38 featuring the valvar mechanism in reversed configuration 42' so that when fully deployed the expanded valved stent FIG. 7B will be oriented to function in the same manner since the final locus is the same, the blood flow is same and only the approach has been reversed, namely the approach from the ventricular side of the mitral annulus. This may be needed when the approach to the target area in the mitral apparatus is made through the tip of the heart or apex, that is when a trans-apical implantation or retrograde (against the normal flow of blood) is sought, and the extended positioning elements or anchors 43 and 44 are deployed sequentially. However, in the expanded configuration, the valved stent returns to the diffuser or truncated cone geometry with a fully coapting valve within. The protrusion or extension of the stent into the left atrium and the ventricle is minimal and pose no hemodynamic alterations particularly from possible encroachment of the left ventricular outflow tract.

The means for anchoring the valve stent (FIG. 5A) provided by the paired winglet will not only serve to maintain said valved stent in place at the shared border of both atrium and ventricle and capturing all tissue material located between an will provide sufficient material between stent and annulus for sealing of the periphery. The anchoring means also maintain the annulus at its dimension at the time of its capture and prevent further dilatation, as papillary muscles do not pull apart from each other and mitral regurgitation is alleviated and ablated. The cyclic effects of the MR condition by continued dilatation of the annulus and base of the heart are impeded so the heart may slowly return, when possible, to normalcy. The ventricular anchors are then restrictors of progression of annular dilatation.

Figure 8:
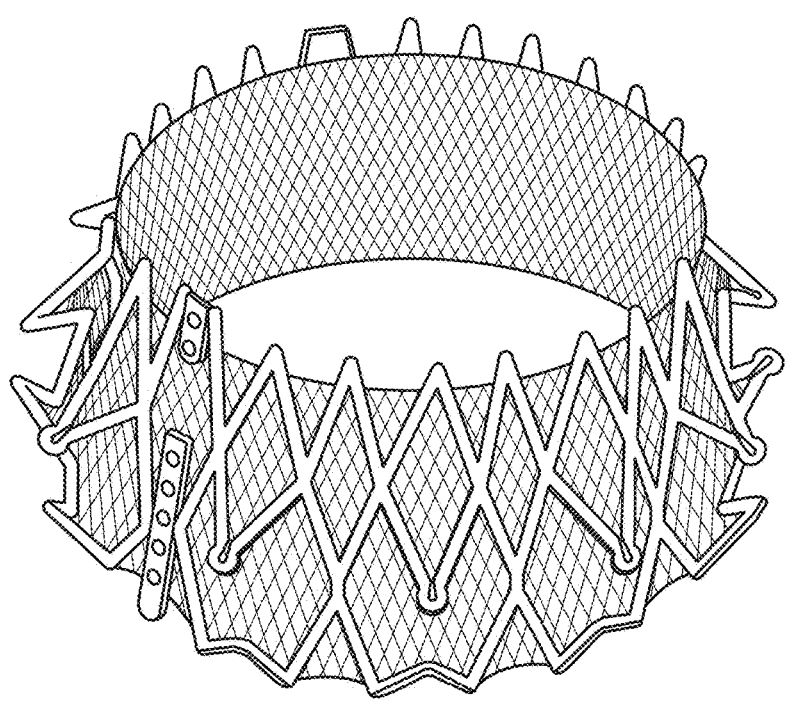
FIG. 8 shows the assembled stent having an inner surface comprised of a microwoven fabric, vertical bars and extending eyelets for attachment to a delivery device.
Figure 9A:
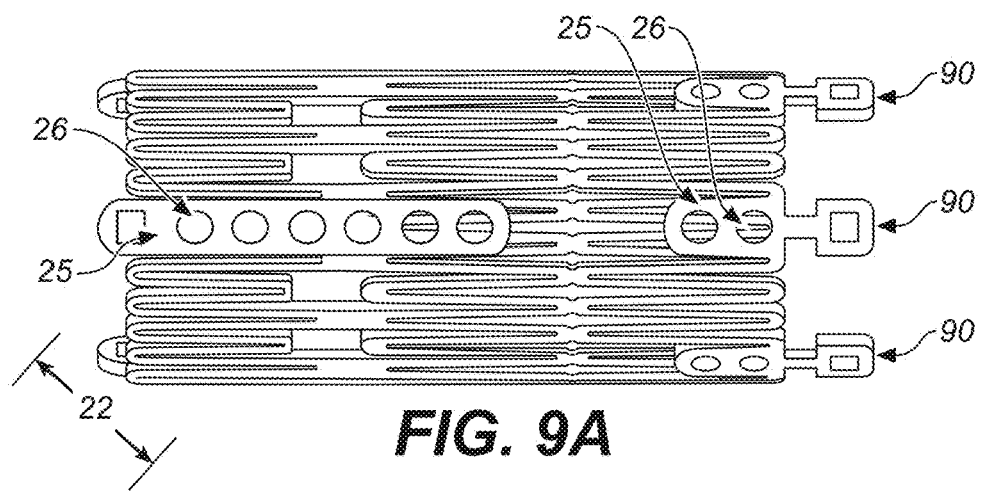
FIGS. 9A-9C are varying designs and orientations of the collapsed stent structure as prepared for enclosure within the delivery system.
Figure 9B:
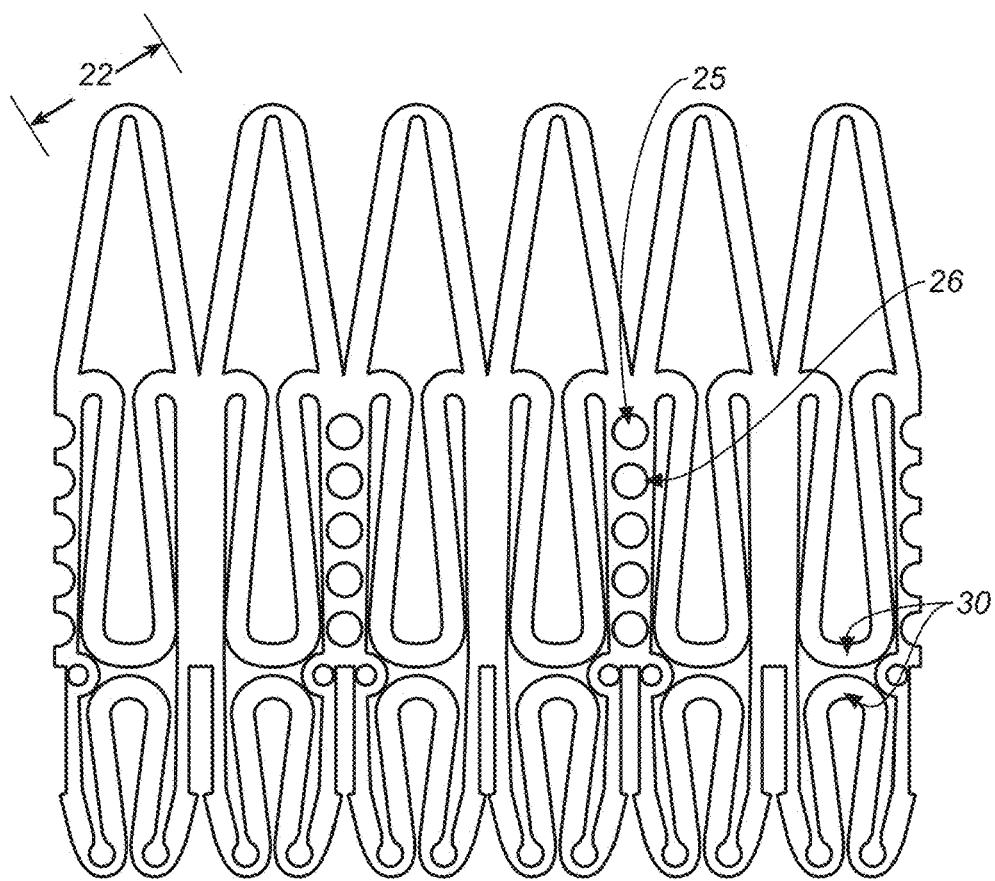
Figure 9C:
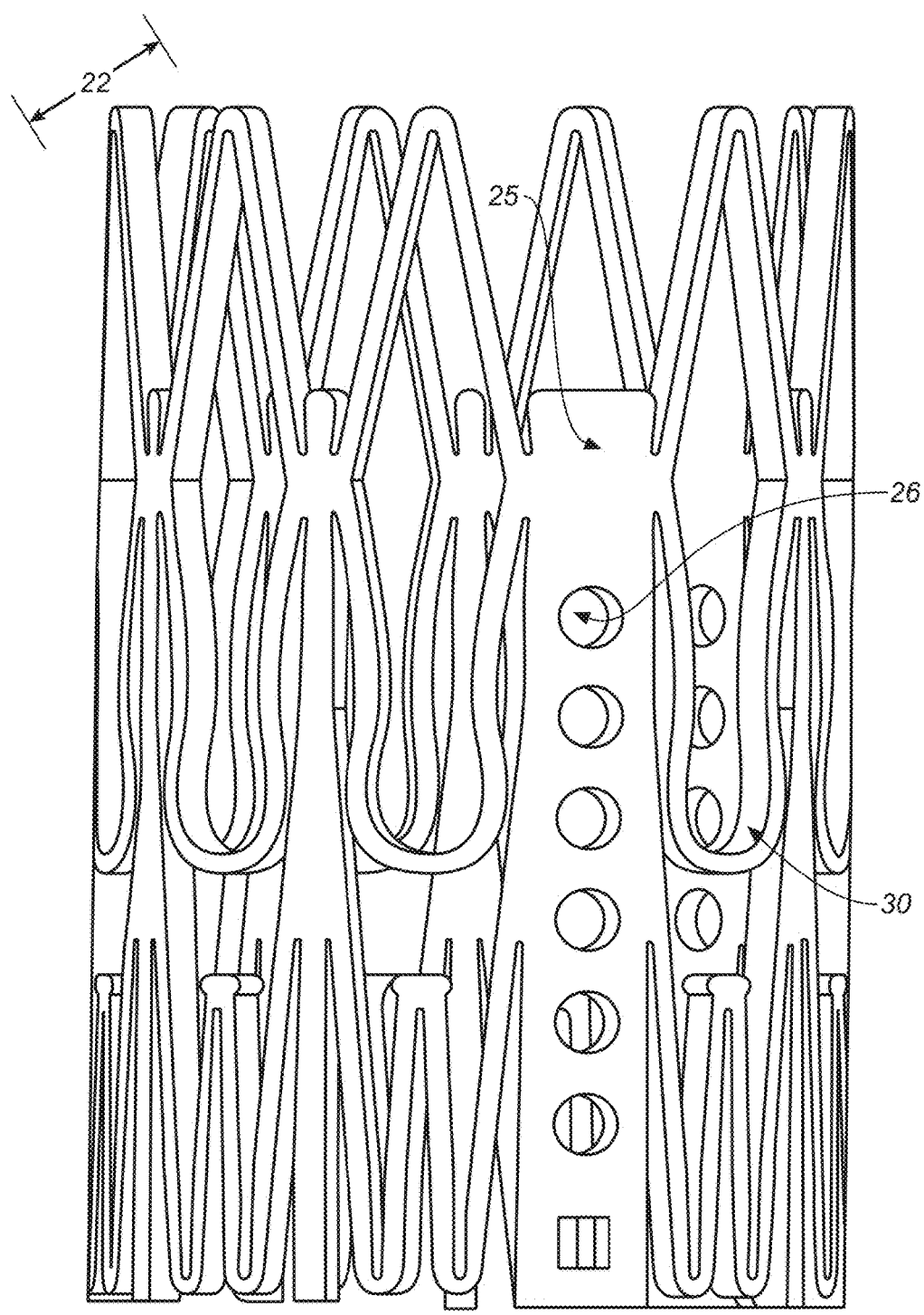
Figure 9D:
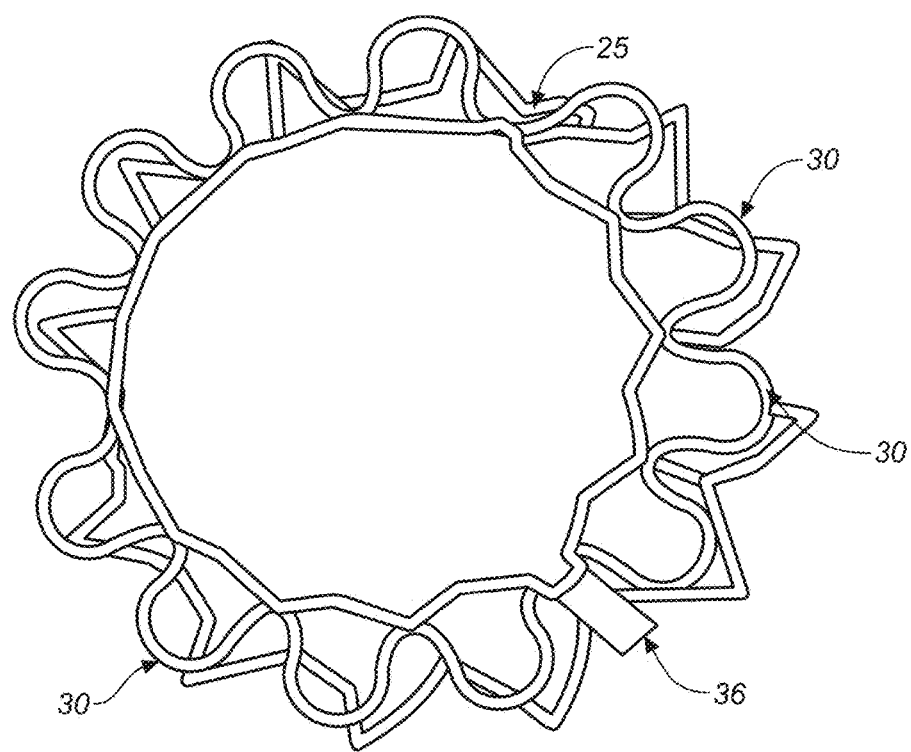
FIG. 9D is the expanded version of the stent structure of FIG. 9C.

FIG. 8 shows the placement of the U-clip that forms and supports the membrane that constitutes the leaflet commissures and the coaptation of the individual leaflets. As shown in FIGS. 5B and 5C, the clip is fixed to the circumferential aspect of the individual membrane section proximate to the joinder of the two adjacent membrane sections and at the outermost portion thereof but interior to the polymeric membrane.

FIG. 9 shows the stent structure replacement valve in a collapsed configuration. The side bars extending both above and below the inflow and outflow aspect in the collapsed configuration.

Figure 10:
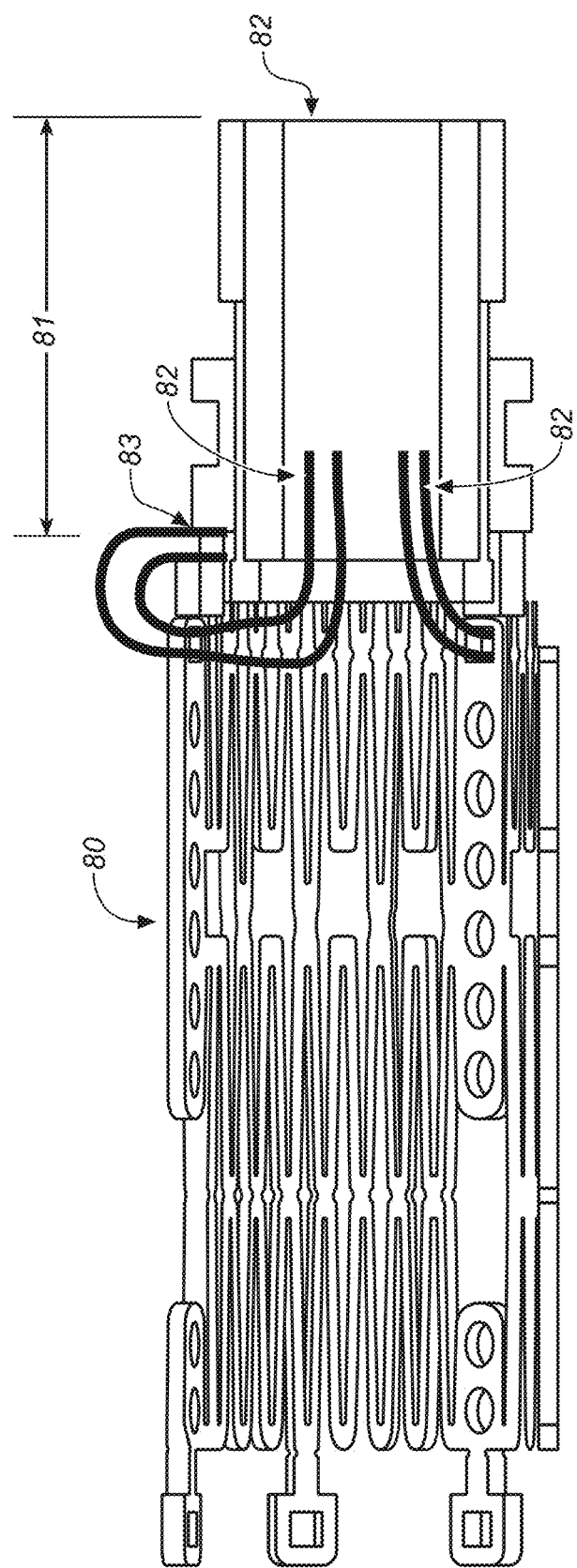
FIG. 10 shows the distal end of the delivery system comprising a cylindrical holder and containing the stent structure of FIG. 9 deployed therein.

FIG. 10 shows a delivery system having a holder such that the stent structure is confined within the holder 80 at a distal portion of the delivery system. Two sutures 82 extend the length of the delivery system and form a loop 83 at the distal end. The loop 83 is threaded through the eyelets that are formed in the side bars and are connected to the holder portion of the delivery system. The holder portion is a cylindrical structure shaped to confine the stent in the collapsed configuration.

Figure 11:
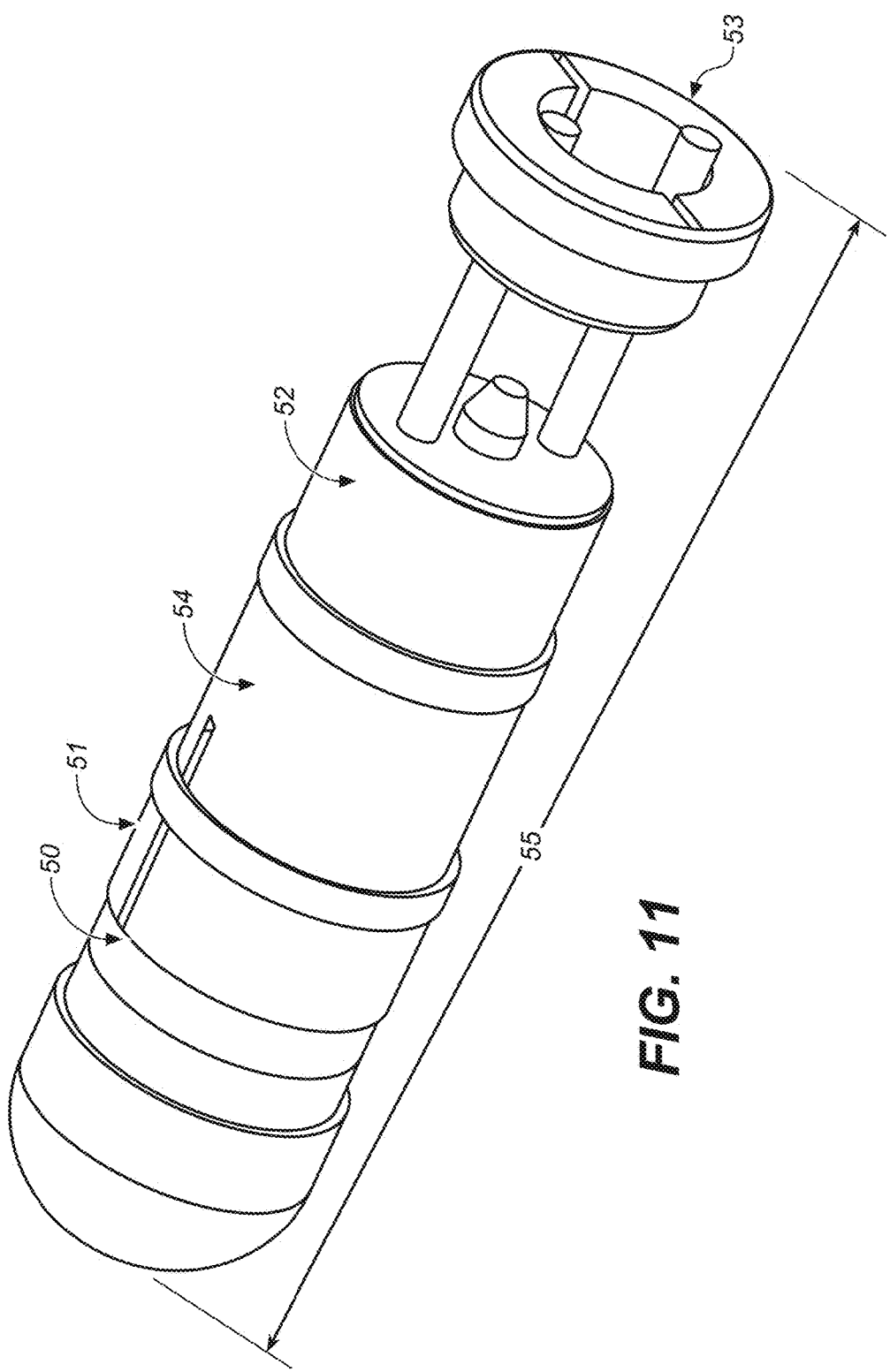
FIG. 11 is the capsular device.

Referring to FIG. 11, the distal sleeve 50 is surrounded by a pull ring 51 of metal such as stainless steel, nitinol alloy, or rust free metallic alloys, of a determined dimension closely fitting the distal sleeve 50 and engaged onto it so that any traction exerted on the pull ring 51 will also retract the distal sleeve 50 in the direction of the crown 52 and hub 53, thus carrying with it the cover of the stent 1 or valved stent.

The length of the metal ring 54 is predetermined to be of the same dimension as the dimension or span existing between the tips of the superior inflow or atrial wing tips or tines, and the inferior, outflow or ventricular wing tips or tines in the stent 2 or mitral valved stent when the stent 1 or valved stent is fully extended or returned to its original nominal dimensions and geometry as shown in FIG. 5. The principal function of the pull ring 51 is to create a uniform pull to retract the distal sleeve 50. This pulling action, performed from outside the body, confirms to the operator that the distal sleeve 50 is being pulled and retracting thus freeing the distal or outflow part of the stent that begins self-expansion in the selected portion of the target site. The greater portion of the valved stent 1 is still held within the capsular device. (See FIG. 11). A particular feature of this pull ring 51 in the capsule device 55 is to serve as a marker defining the annular gap of the stent 1 or valved stent device, and said annular gap represents the grasping sector of the valved stent 1 as is required to gain hold of the selected portion of the target site at the native cardiac valve annulus where the valve stent 1 will anchor.

Prior to applying traction to this pull ring 51, the pull ring 51 can be imaged by various imaging techniques such as fluoroscopy (x-rays) or echocardiography (intracardiac echo ICE, or transthoracic echo TTE or transesophageal echo TEE). In this manner, the annular sector of the valved stent 1 can be oriented and practically superimposed with the native mitral valve annular plane or its surrounding environs to ensure that there the mitral valved stent 38 securely holds the native valve structures. The capsular device 55 provides means for continuous and total control of the deployment and delivery of the valved stent 1 into the diseased valve. In contrast, the existing self-expanding valves, because the self-expanding portion of the valve is the stent, will always expand as the stent expands, without control of the rate or extent of expansion and risks inaccurate positioning in the surrounding native valve environs. The capsular device 55 obviates the abrupt one-step expansion experienced with existing self-expanding valved stents.

Figure 12:
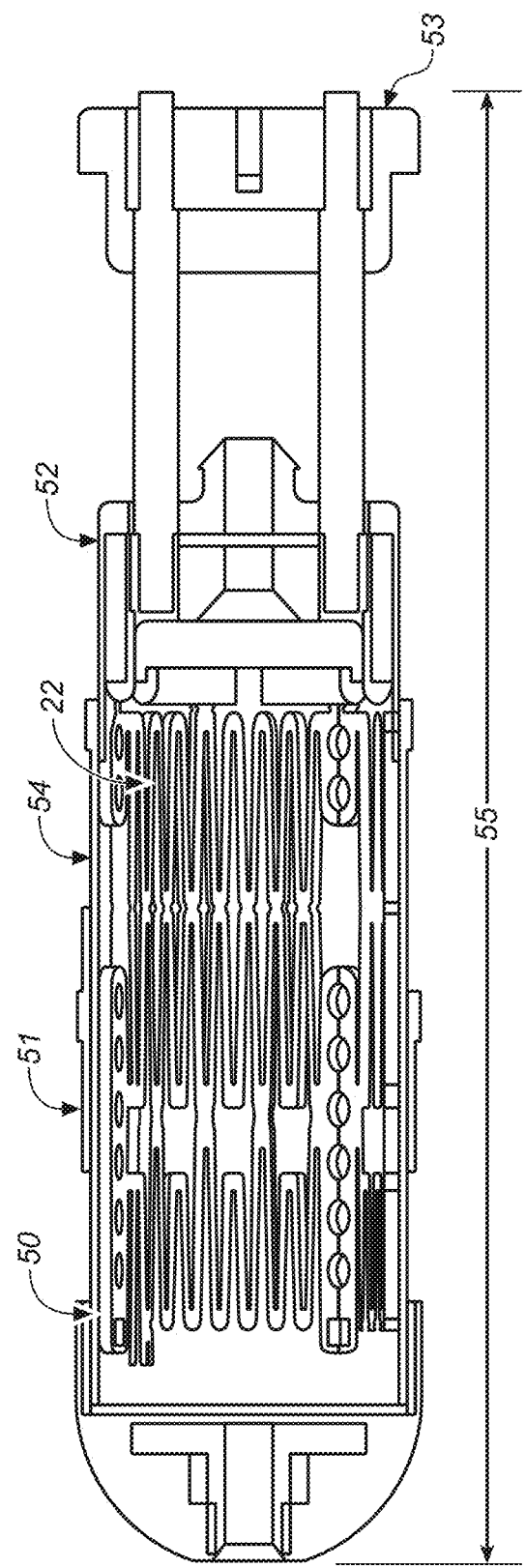
FIG. 12 is a cut away view of the capsular device with the stent in the compressed configuration.

Referring to FIG. 12, the capsular device 55 has inner structures necessary to enclose the constricted mitral valved stent in its entirety and keep it from expanding while in the enclosure even when temperatures exceed the transition temperatures of the shape memory metal. The capsule wall is such that the mitral valved stent 3 is kept in its cylindrical geometry within the capsular device. As noted above, the placement of the valved stent can be achieved by either the cranial or caudal direction. The capsular device 55 is particularly useful when the stent landing zone is approached from the cranial (from above) direction of the native mitral valve. The contracted or crimped mitral valved stent 1 is placed within the capsular device 55 with its superior aspect or in case of the mitral valve, the atrial truncated conical aspect having the smallest diameter inserted into the capsular device in such a manner that said mitral valved stent protruding members bearing the six or more eyelets.

Figure 13:
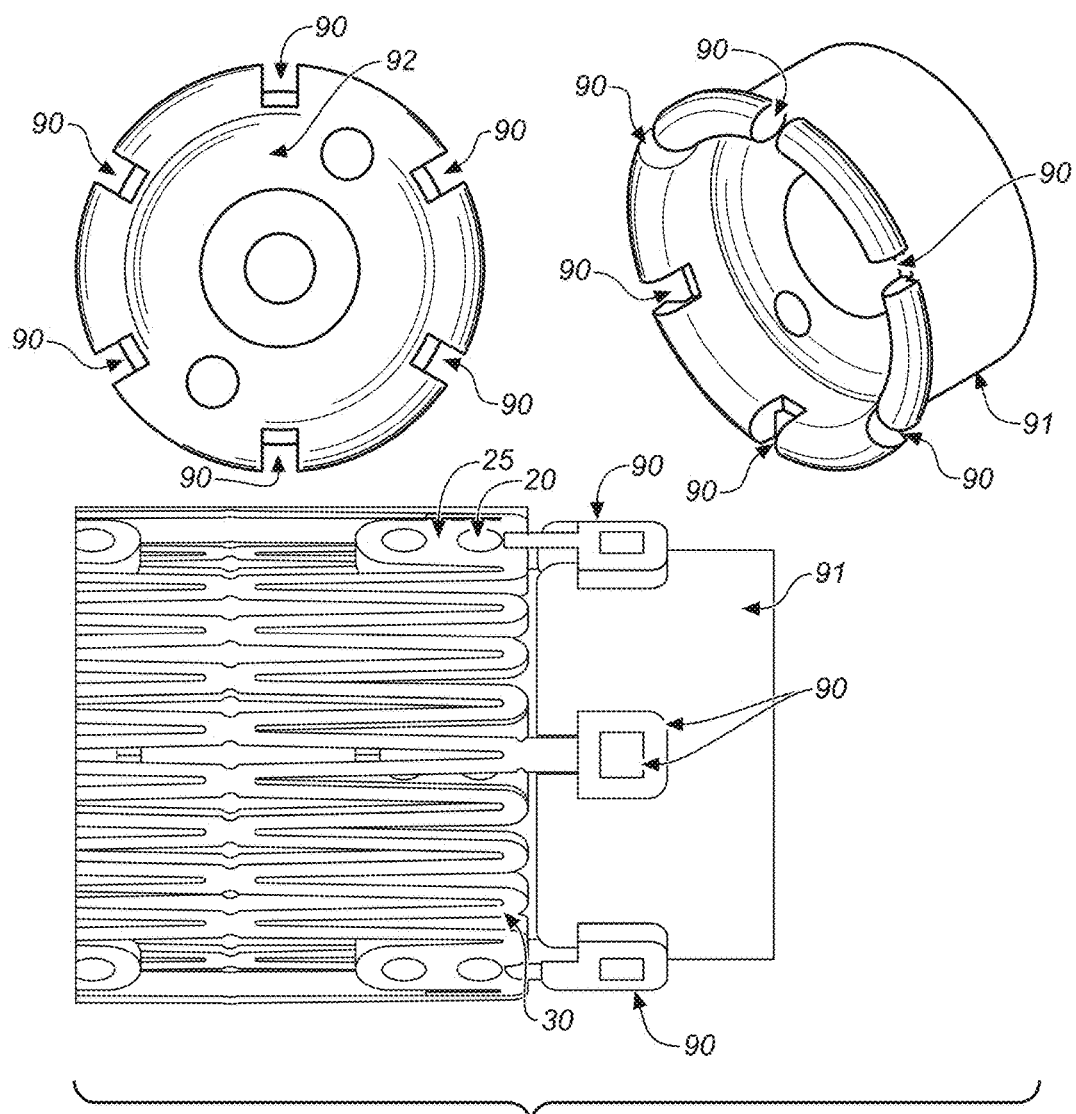
FIG. 13 shows the engagement of the eyelets with the distal end of the holder.

Referring to FIG. 13, the eyelets engage the crown 52 such that the eyelets meet matching members within the crown 52 that are extending from a short cylindrical structure in the form of a circular plate. Said members will snap by interference fit into the eyelets 90 of the mitral valved stent and thus produce a hold of the valved stent 38 through the eyelets between the capsule inner wall and the short cylindrical plate structure.

The cylindrical plate structure 60 while within the capsular enclosure 55, can be itself part of a shaft or a catheter that can be used to push said cylindrical structure 58 forwards from the crown 52 and backwards after the forward push but not backwards from its initial seating in the crown 52. In this manner, the operator outside the body pushes the valved stent 1 after the distal or center sleeves 50, 54 are retracted and the valved stent outflow (larger diameter or truncate conical structure) expands to a fraction of the diameter. The expansion is not complete because the short cylindrical plate 60 while still within the capsule 55 will continue to hold the stent 1 through the eyelets 40 so long as the plate 60 is within the capsule 55. The stent 1 is snapped and locked onto the cylindrical plate 60 but either a push or a retraction of the capsular wall away from the plate 50 will allow the captured eyelets 10 to snap free from the plate protrusions and become free from the capsular device 55.

Employing the cranial approach to the mitral valve placement, the caudal aspect of the valved stent is released first such that the ventricular or lower tines or winglets 10 will be first to expand. The control of that expansion is limited by the sleeves 50, 54 of the capsule 55. Thus only a fraction of the valved stent 1 will be expanded when the distal sleeve 50 is retracted, that is only a fraction of the valved stent 1 outflow circumference (diameter) will be expanded. As the central sleeve 54 is retracted, the distal circumference increases and approaches its nominal diameter during expansion, the valve stent achieves a grasping action over the native mitral leaflets. The atrial or upper, superior tines or winglets 10 have then began to expand, but the atrial diameter, or stent superior aspect diameter has the diameter of the capsule device 55 since it is still held between the inner wall of and the cylindrical plate 60 of the holder. This allows the operator from a substantial distance and with imaging to control the position of the grasping function and gap generated by the valved stent 38 expansion to capture the native annular plane tissue and leaflet tissue to provide a secure fixation valved stent 38 in its proper position at the target site. In contrast, the valves designed to correct aortic stenosis, where the existing valves use radial force and friction by expansion to fit into the calcific valve. In cases where a valve annulus has become dilated and expanded producing valvular incompetence, radial force and friction only further expand the diameter of the native valve and the replacement is able to effectively hold and seal the orifice correct the incompetence.

Accordingly, and to reach the ideal exemplary embodiment in this disclosure of said mitral valved stent device and its effective use in essence and form, a complementary device must be designed that will with the valved stent accomplish both the accurate placement and allowance of proper function of the disclosed valved stent. For most of the embodiments of the mitral valved stent said device forms an inseparable part or complement of the mitral valved stent (MVS) if the latter will be able to accomplish its intended function adequately. Said device will aid the valved stent to assume various forms to allow it to reach the intended landing zone and simultaneously allow metamorphosis necessary for navigation through vasculature and cardiac structures of the biological organisms or systems in which it will reside finally to perform its intended function.

In its contracted state, the mitral valved stent has been forced to adopt the form of a cylindrical tube by specific means although proceeding from a truncated cone. FIG. 13 is a drawn representation of said contracted stent wherein at its superior aspect the stent or the valved stent features six or more extended bars with eyelets or perforations of specific shape which can be engaged by specifically equally shaped protrusions of a separate device, a holder, said engagement serving to hold the superior aspect of the stent within a closely fitting cylindrical capsule formed by telescoping sliding cylinders or sleeves, the distal sleeve larger than the central sleeve and said central sleeve larger than the proximal sleeve or crown. All this mechanism is secured at one end to a hub but free and unattached at the opposite end, and the stent or valved stent is there to reside until it is decided to uncover the separate or holding device so to reach the free end of the capsule. To ensure that coaxial motion is maintained, two alignment rods connecting hub and the stent or valved stent capsule device form part and maintain hold of the stent or valved stent device pod or capsule. In this manner, the stent or valved stent slowly and in a direct manner resumes partly its original truncated conical shape, while still being held onto the crown until having reached what is considered the proper position of the mitral valved stent and it can be released so the winglets or tines can grasp the surrounding area of the native mitral valve annulus and mitral leaflets joints.

The distal sleeve is surrounded by a pull ring of metal such as stainless steel, nitinol alloy, or rust free metallic alloys, of a determined dimension closely fitting the distal sleeve and engaged onto it so that any traction exerted on the pull ring will also retract the distal sleeve in the direction of the crown and hub, thus carrying with it the cover of the stent or valved stent.

Referring again to FIGS. 12 and 13, the superior aspect of the expanded contracted stent or the valved stent 1 features six or more extended bars with eyelets or perforations of specific shape which can be engaged by specifically equally shaped protrusions of the holder, said engagement serving to hold the superior aspect of the stent 1 within a closely fitting cylindrical capsule 55 formed by telescoping sliding cylinders 50,54 or sleeves 91,92, the distal sleeve 91 being larger than the central sleeve 92 and said central sleeve 92 being larger than the proximal sleeve or crown 6. All this mechanism is secured at one end to a hub 53 but free and unattached at the opposite end, and the stent 1 or valved stent assembly resides until the separate holding device is actuated to reach the free end of the capsule 55. To ensure that coaxial motion is maintained, two alignment rods (See FIG. 11) connecting hub 53 and the stent 1 or valved stent capsule device form part and maintain hold of the stent 1. In this manner, the stent 1 or valved stent is selectively expanded in a directed manner to partly resume the original truncated conical shape, while still being held onto the crown until having reached the proper position of the mitral valved stent within the native annulus. By this design, the apparatus is incrementally positioned by first, partially expanding the structures, followed by deployment such that the winglets 10 can grasp the surrounding area of the native mitral valve annulus and mitral leaflets joints.

What is claimed is:

1. A bioprosthetic heart valve assembly having a geometric configuration for implantation in an annulus of the native heart valve comprising: a) a tubular structure having an entry opening end and an exit opening at opposite ends thereof, wherein the tubular structure is comprised of an expandable stent structure comprised of a plurality of interconnected elements having a compressed configuration and an expanded configuration and wherein a plurality of the elements are comprised of winglets that extend away from the external circumferential surface of the stent in the expanded configuration and wherein the stent member is comprised of a plurality of vertical bars having eyelets at the end thereof; b) a biocompatible material covering a substantial portion of an inner annular region between the entry opening and the exit opening, c) a valve comprised of a plurality of leaflets capable of forming a fluid tight seal at the apposing edges thereof wherein the circumference of the plurality of leaflets together form a fluid tight seal about an interior of the valve assembly between the entry opening and the exit opening, wherein the tubular structure has a tapered diameter along a length thereof such that the entry opening and the exit opening have different diameters and d) a holder affixed to the stent member in the compressed configuration, wherein the eyelets engage a fixture on an interior portion of the holder.

2. A bioprosthetic heart valve assembly having a geometric configuration for implantation in an annulus of the native heart valve comprising: a) a tubular structure having an entry opening end and an exit opening at opposite ends thereof, wherein the tubular structure is comprised of an expandable stent structure comprised of a plurality of interconnected elements having a compressed configuration and an expanded configuration, wherein the expandable stent and the valve are maintained in a compressed configuration in the interior of a capsular device having a sleeve covering at least a portion of an axial length of the tubular structure and wherein a plurality of the elements are comprised of winglets that extend away from the external circumferential surface of the stent in the expanded configuration; b) wherein the expandable stent and the valve are maintained in a compressed configuration in the interior of a capsular device having a sleeve covering at least a portion of an axial length of the tubular structure, wherein the capsular device is comprised of a plurality of sleeves having different diameters and disposed concentrically and at least one sleeve is concentric and slidable around another, and a biocompatible material covering a substantial portion of an inner annular region between the entry opening and the exit opening, and c) a valve comprised of a plurality of leaflets capable of forming a fluid tight seal at the apposing edges thereof wherein the circumference of the plurality of leaflets together form a fluid tight seal about an interior of the valve assembly between the entry opening and the exit opening, wherein the tubular structure has a tapered diameter along a length thereof such that the entry opening and the exit opening have different diameters.

3. A bioprosthetic heart valve assembly having a geometric configuration for implantation in an annulus of the native heart valve comprising: a) a tubular structure having an entry opening end and an exit opening at opposite ends thereof, wherein the tubular structure is comprised of an expandable stent structure comprised of a plurality of interconnected elements having a compressed configuration and an expanded configuration and wherein a plurality of the elements are comprised of winglets that extend away from the external circumferential surface of the stent in the expanded configuration; b) a biocompatible material covering a substantial portion of an inner annular region between the entry opening and the exit opening, and c) a valve comprised of a plurality of leaflets capable of forming a fluid tight seal at the apposing edges thereof wherein the circumference of the plurality of leaflets together form a fluid tight seal about an interior of the valve assembly between the entry opening and the exit opening, wherein the tubular structure has a tapered diameter along a length thereof such that the entry opening and the exit opening have different diameters and d) a holder disposed at the distal end of a catheter, wherein the stent member is releasably attached to a distal end of the holder and held in a configuration that is partially expanded.

4. The bioprosthetic valve assembly of claim 3, wherein stent member is releasably attached to the holder at the entry opening.

5. The bioprosthetic heart valve assembly of claim 3, wherein the stent member is releasably attached to the holder at the exit opening.

* * * * *